United States Patent
Sharma et al.

(10) Patent No.: US 11,078,535 B2
(45) Date of Patent: Aug. 3, 2021

(54) PRESYMPTOMATIC MICRO RNA TARGETS FOR TREATMENT OF NEURODEGENERATION PATHOLOGY

(71) Applicant: The Trustees of Indiana University, Indianapolis, IN (US)

(72) Inventors: Salil Sharma, Bloomington, IN (US); Hui-Chen Lu, Bloomington, IN (US)

(73) Assignee: The Trustees of Indiana University, Indianapolis, IN (US)

( * ) Notice: Subject to any disclaimer, the term of this patent is extended or adjusted under 35 U.S.C. 154(b) by 0 days.

(21) Appl. No.: 16/631,866

(22) PCT Filed: Jul. 7, 2018

(86) PCT No.: PCT/US2018/042434
§ 371 (c)(1),
(2) Date: Jan. 17, 2020

(87) PCT Pub. No.: WO2019/018361
PCT Pub. Date: Jan. 24, 2019

(65) Prior Publication Data
US 2020/0157627 A1    May 21, 2020

Related U.S. Application Data

(60) Provisional application No. 62/665,888, filed on May 2, 2018, provisional application No. 62/660,030, filed on Apr. 19, 2018, provisional application No. 62/533,870, filed on Jul. 18, 2017.

(51) Int. Cl.
| | |
|---|---|
| *A61P 25/28* | (2006.01) |
| *C12N 15/113* | (2010.01) |
| *C12Q 1/6883* | (2018.01) |
| *A61K 31/7105* | (2006.01) |
| *C12Q 1/686* | (2018.01) |

(52) U.S. Cl.
CPC ........ *C12Q 1/6883* (2013.01); *A61K 31/7105* (2013.01); *A61P 25/28* (2018.01); *C12N 15/113* (2013.01); *C12Q 1/686* (2013.01)

(58) Field of Classification Search
None
See application file for complete search history.

(56) References Cited

U.S. PATENT DOCUMENTS

| | | | |
|---|---|---|---|
| 2011/0262387 A1* | 10/2011 | Das | A61P 25/28 424/85.2 |
| 2014/0235697 A1 | 8/2014 | Weiner | |
| 2014/0378439 A1 | 12/2014 | Dezso | |
| 2017/0137813 A1 | 5/2017 | Xu | |

FOREIGN PATENT DOCUMENTS

| | | |
|---|---|---|
| WO | 2013/134403 | 9/2013 |
| WO | 2015/006705 | 1/2015 |

OTHER PUBLICATIONS

Anthony King Nature vol. 559 pp. S13-S15 (Year: 2018).*
Jankowksy et al. Molecular Neurodegeneration 12:89, pp. 1-22 (Year: 2017).*
International Search Report and Written Opinion; International Application No. PCT/US18/42434 dated Oct. 1, 2018.

* cited by examiner

*Primary Examiner* — Brian Whiteman
(74) *Attorney, Agent, or Firm* — Barnes & Thornburg LLP

(57) ABSTRACT

Compositions and methods are provided for the early detection of neuroinflammation in a patient in a presymptomatic stage of a neurodegenerative disease. The method comprises identifying patients with elevated expression levels of a micro RNA selected from the group consisting of miR142-3p, miR142-5p, miR181a, miR181b, miR219-3p and miR219-5p. The identified patients can then be treated with a therapeutic pharmaceutical composition comprising anti-miR oligonucleotides.

3 Claims, 3 Drawing Sheets
Specification includes a Sequence Listing.

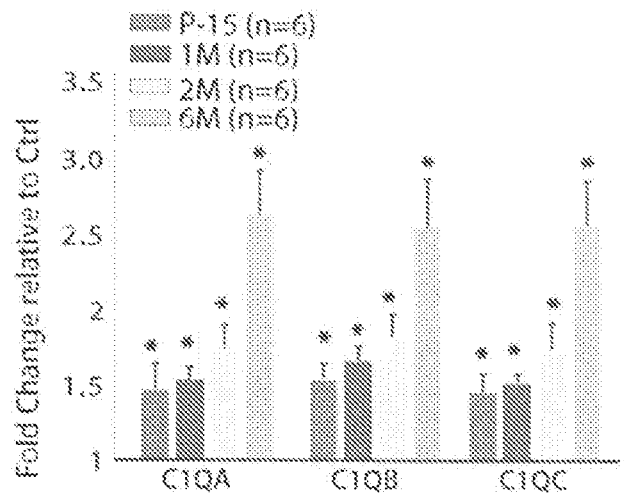
Fig. 4
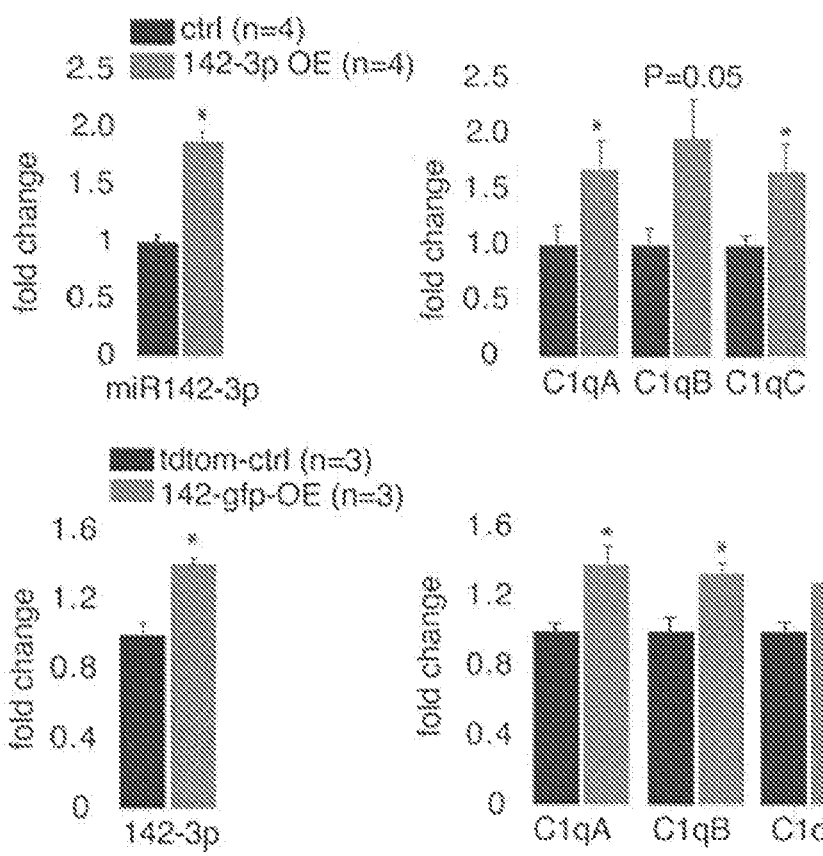
Fig. 5A
Fig. 5B

PRESYMPTOMATIC MICRO RNA TARGETS FOR TREATMENT OF NEURODEGENERATION PATHOLOGY

CROSS REFERENCE TO RELATED APPLICATIONS

This application is a 371 national stage application of PCT/US2018/042434 which claims priority to the following: U.S. Provisional Patent Application No. 62/533,870 filed on Jul. 18, 2017, U.S. Provisional Patent Application No. 62/660,030 filed Apr. 19, 2018, and U.S. Provisional Patent Application No. 62/665,888 filed on May 2, 2018. The disclosure of each application is hereby expressly incorporated by reference in its entirety.

STATEMENT OF GOVERNMENT SUPPORT

This invention was made with government support under grant no. NS086794 awarded by the National Institutes of Health. The Government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 7 kilobytes ACII (Text) file named "279908SeqListing.txt," created on Jul. 11, 2018.

BACKGROUND OF THE DISCLOSURE

MicroRNAs (miRs) constitute an abundant class of non-coding RNA molecules that are endogenously expressed in multicellular organisms. They are typically 18-23 nucleotides long, and often regulate gene expression by mRNA degradation or translational repression. Many miRs are enriched in brain, and contribute to brain development, neural plasticity and neuroprotection. Interestingly, the levels of many miRs are altered in neurodegenerative diseases. For example, Lau et al (EMBO Mol Med 5, 1613-1634 (2013)) identified 35 miRs altered in the prefrontal cortex of late-onset Alzheimer's Disease (LOAD) patients. Furthermore, Lau et al reported that deleting Dicer, a critical enzyme involved in miR synthesis, in adult brain results in Tau hyperphosphorylation and neuronal loss, with the pathological phenotypes associated with tauopathy, manifested as deposition of intracellular neurofibrillary tangles. However, it is unclear whether miR changes are already present at the presymptomatic stages of neurodegenerative diseases, and if such miR changes can directly impact biological pathways that may subsequently lead to neurodegeneration.

Tauopathies include a wide range of neurodegenerative diseases such as progressive supranuclear palsy, Pick's disease, parkinsonism linked to chromosome 17 (FTDP-17) and Alzheimer's disease (AD). Previously, miRs have been identified as modulators of Tau, and contribute to Tau pathology (see Wang, G. et al. Sci Rep 6, 26697, (2016). Santa-Maria et al showed that Tau is one of the direct targets of miR219 (J Clin Invest 125, 681-686, (2015). MiR219 downregulation aggravated Tau induced toxicity, whereas its overexpression alleviated the toxic effects. Therefore, miR219 expression may modulate Tau toxicity by post-transcriptionally repressing Tau expression. In AD brains, miR132-3p levels are mainly decreased in neurons enriched with hyper-phosphorylated Tau. Several genes implicated in Tau network, including the transcription factor (TF) FOXO1a, were identified as miR132-3p targets by in silico methods. Knocking out the miR132/212 cluster results in an increase in Tau phosphorylation and aggregation. Consistent with previous studies, genome-wide studies using 39 AD and 25 control brains found significant downregulation of miR132/212 cluster in AD temporal cortex (TC).

Tauopathies, which involve deposition of intracellular neurofibrillary tangles arising from mutations, hyperphosphorylation and misfolding of microtubule associated protein tau (MAPT), are implicated in the pathogenesis of neuroinflammation. Tauopathies comprise a wide range of neurodegenerative diseases, including Alzheimer's disease. As of 2017, an estimated 5.5 million Americans have Alzheimer's disease, and it is the sixth leading cause of death with an estimated cost of 259 billion. Sadly, no curative treatments are currently available. Therefore, there is an urgent need to develop therapeutic agents to diagnose, cure and/or mitigate this fatal disease and other neurodegenerative diseases, disorders and conditions.

MiRs have emerged as potent regulators of many gene expression pathways altered in neurodegenerative diseases. Particularly, in tauopathies, miRs have been identified as modulators of tau, and thereby contribute to tau pathology. MiRs regulate gene expression by mRNA degradation or translational repression. MiRs can target several genes, and are involved in both physiology and disease states.

The present disclosure is directed to the use of miRs as a therapeutic target to develop effective RNA-based therapeutic interventions to mitigate neuroinflammatory responses triggered by protein aggregates in the brain. Accordingly, the present disclosure is directed to measuring both miR and mRNA changes at presymptomatic stage of tauopathy and devising strategies for diagnosing and treating neurodegeneration at an early stage. In one embodiment, miR-RNA pairing analysis was conducted to identify putative miR targets. Therapeutic strategies will be implemented, including for example the use of antisense technologies against target miRs, to modulate miR activities and treat neurodegenerative diseases.

SUMMARY

The present disclosure relates generally to the use of microRNAs (miRs) as therapeutic targets to develop effective RNA-based therapeutic interventions to diagnose and treat neurodegenerative diseases and/or psychiatric disorders. In one aspect of the invention, the present disclosure has identified miRs selected from the group consisting of miR142-3p, miR142-5p, miR181a, miR181b, miR219-3p and miR219-5p as being upregulated in the hippocampi of animal models of neurodegeneration. Using in vitro neuronal cultures and in-vivo animal models, the present disclosure shows that miR-142 gain of function can target many genes including complement proteins (i.e., C1qA, C1qB and C1qC) involved in neuroinflammation as well as other biological pathways.

In one embodiment, the present disclosure relates to the use of miRs selected from the group consisting of miR142-3p, miR142-5p, miR181a, miR181b, miR219-3p and miR219-5p, as biomarkers for the development of neuroinflammation and neurodegenerative diseases. In one embodiment, the present disclosure relates to the use of miR-142 or miR181, and more particularly, miR-142-5p and miR-142-3p, as biomarkers for the development of neuroinflammation and neurodegenerative diseases, as well as to the use of antisense technologies against miR181 or miR-142 for the treatment of neurodegenerative diseases (e.g., Alzheimer's disease) and/or psychiatric disorders (e.g., schizophrenia).

In one embodiment a method of detecting neuroinflammation in a patient who is presymptomatic for a neurodegenerative disease is provided. The method comprises obtaining a reference expression level of one or more miRs selected from the group consisting of miR142-3p, miR142-5p, miR181a, miR181b, miR219-3p and miR219-5p; determining an expression level of the corresponding one or more miRs selected from the group consisting of miR142-3p, miR142-5p, miR181a, miR181b, miR219-3p and miR219-5p in a sample obtained from the patient, wherein an increase in the expression level of one or more miRs selected from the group consisting of miR142-3p, miR142-5p, miR181a, miR181b, miR219-3p and miR219-5p in the sample obtained from the patient, as compared to the reference expression level, indicates neuroinflammation. In one embodiment the miRs are selected from the group consisting of miR142-3p, miR142-5p, miR181a, and miR181b. In one embodiment the detected miR is miR-142, and more particularly an miR-142 selected from the group consisting of miR-142-3p, miR-142-5p and combinations thereof.

In one embodiment a method of treating a neurodegenerative disease in an patient in need thereof is provided. In one embodiment the method comprises a first step of identifying patients suffering from neuroinflammation even when they are presymptomatic for a neurodegenerative disease. The method is based on the identification of elevated miR levels in said patient. Patients identified with elevated expression levels of one or more miRs selected from the group consisting of miR142-3p, miR142-5p, miR181a, miR181b, miR219-3p and miR219-5p are treated by administering a pharmaceutical composition that reduces the expression level of one or more miRs selected from the group consisting of miR142-3p, miR142-5p, miR181a, miR181b, miR219-3p and miR219-5p. In one embodiment the expression level of one or more miRs (e.g., miR-142) is reduced by administering to the patient an RNA-based antisense oligonucleotide, or interference RNA, complementary to the relevant miR nucleotide sequence, selected from the group consisting of miR142-3p, miR142-5p, miR181a, miR181b, miR219-3p and miR219-5p, optionally miR142.

BRIEF DESCRIPTION OF THE DRAWINGS

FIG. 1A is a bar graph providing the different expression of each miR at 15 days (P-15), 1 month (1 Mo), 2 month (2 Mo), and 6 month (6 Mo), postnatal. In addition to hippocampus, miR142-3p expression is also induced in Tau mice cortex at 2 m and 6 m (see FIG. 1B).

FIG. 4 depicts qPCR validation showing upregulation of complement proteins in tau mice hippocampi at early to late time points.

FIGS. 5A & 5B show the effect of miR-142-3p overexpression (OE) on complement expression. FIG. 5A presents data demonstrating that in vitro miR-142-3p overexpression (OE) in neurons resulted in an increase in complement mRNAs.

FIG. 5B presents data demonstrating that in vivo miR-142-3p OE in mice resulted in an increase in complement mRNAs.

DETAILED DESCRIPTION

Definitions

Figure 1A:
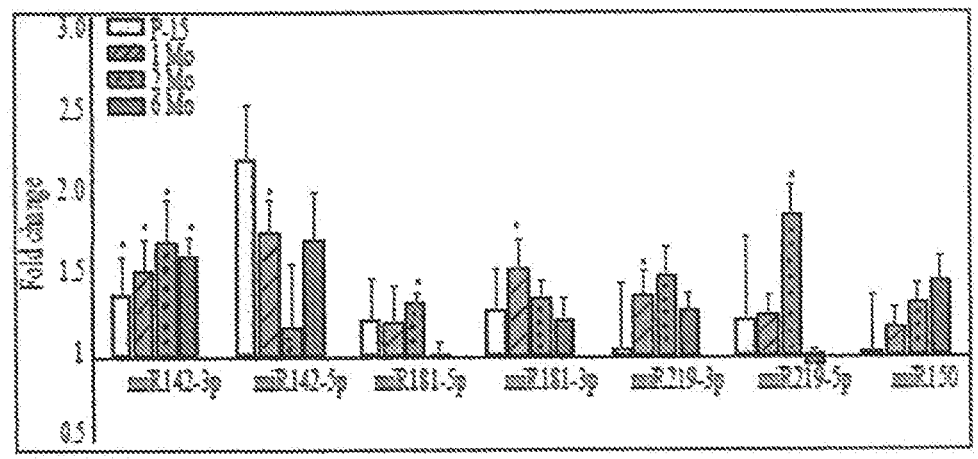
FIGS. 1A & 1B depicts age-dependent changes in miRs in the plasma and hippocampus of tau mice as analyzed in Example 1. Levels of miR-142 (-3p and -5p), miR-181 (-3p and -5p), miR219 (-3p and -5p) and miR-150 were detected in mouse hippocampi both in control and rTg(tauP301L) 4510 (tau mice) mice using real-time PCR (qPCR).

In describing and claiming the invention, the following terminology will be used in accordance with the definitions set forth below.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

As used herein, the term "treating" includes prophylaxis of the specific disorder or condition, or alleviation of the symptoms associated with a specific disorder or condition and/or preventing or eliminating said symptoms.

As used herein an "effective" amount or a "therapeutically effective amount" of an interference RNA or antisense RNA mimetic refers to a nontoxic but sufficient amount of the compound to provide the desired effect. For example one desired effect would be the prevention or treatment of a neurodegenerative disease, as measured, for example, by a decrease in nerve tissue death or decrease in Tau concentrations. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as subcutaneous, intramuscular, intraspinal, or intravenous.

As used herein, the term "purified" and like terms relate to the isolation of a molecule or compound in a form that is substantially free of contaminants normally associated with the molecule or compound in a native or natural environment. As used herein, the term "purified" does not require absolute purity; rather, it is intended as a relative definition. The term "purified RNA" is used herein to describe an RNA sequence which has been separated from other compounds including, but not limited to polypeptides, lipids and carbohydrates.

The term "isolated" requires that the referenced material be removed from its original environment (e.g., the natural environment if it is naturally occurring). For example, a naturally-occurring nucleic acid present in a living animal is not isolated, but the same nucleic acid, separated from some or all of the coexisting materials in the natural system, is isolated.

As used herein, "neuroinflammation" and/or "neurodegeneration" refers to the chronic inflammatory response resulting from the deposition of insoluble proteins in the brain. Neuroinflammation often leads to escalating toxicity and neuronal death.

As used herein, "expression level of miR-181" with no further designation refers to the combined expression level of miR-181a and miR-181b.

As used herein, "expression level of miR-142" with no further designation refers to the combined expression level of miR-142-5p and miR-142-3p.

As used herein, "a reference expression level of an miR" (e.g., a reference expression level of miR-142) refers to the expression level of the miR established for an individual with no signs of neurodegeneration, expression level of the miR in a normal/healthy individual diagnostically free of any neurodegenerative disease as determined by one skilled in the art using established methods, and/or a known expression level of the miR obtained from literature.

As used herein, "expression level of C1qA, C1qB, and C1qC" refers to the individual expression level of one or more of C1qA, C1qB, and C1qC. As used herein, "a reference expression level of C1qA, C1qB, and C1qC" refers to the individual expression level of one or more of C1qA, C1qB, and C1qC established for an individual with no signs of neurodegeneration, expression level of one or more of C1qA, C1qB, and C1qC in a normal/healthy individual diagnostically free of any neurodegenerative disease as determined by one skilled in the art using established methods, and/or a known expression level of one or more of C1qA, C1qB, and C1qC obtained from literature.

As used herein the term "tauopathy" encompasses neurodegenerative diseases associated with the pathological aggregation of tau protein in neurofibrillary or gliofibrillary tangles in the human brain.

As used herein, "neurodegenerative diseases" include dementia (e.g., tauopathy, Alzheimer's disease), Picks disease, post-encephalitic Parkinsonism, and any other disease known in the art to involve tauopathy. As used herein, "psychiatric disorders" include schizophrenia.

As used herein the term "patient" without further designation is intended to encompass any warm blooded vertebrate domesticated animal (including for example, but not limited to livestock, horses, mice, cats, dogs and other pets) and humans.

As used herein the phrase "presymptomatic for neurodegenerative diseases" defines a patient's condition wherein the patient has an elevated risk for developing a neurodegenerative disease but has yet to exhibit any symptoms associated with the neurodegenerative disease.

As used herein "an elevated expression of an miR" is considered any detected statistically enhanced expression in a patient's biological sample relative to a referenced level of the corresponding miR based on population data or detected levels in one or more individuals that are free of a neurological disease.

As used herein "an antisense oligonucleotide" or "interference RNA" includes nucleic acid sequences using standard nucleotides and linkages as well an nucleic acid mimetics of nucleic acid sequences. For example most antimiR oligonucleotides will harbor phosphorothioate (PS) backbone linkages, in which sulfur replaces one of the non-bridging oxygen atoms in the phosphate group. Other modified nucleic acid sequences are known to those skilled in the art and are intended to be encompassed by the generic terms of antisense oligonucleotide and interference RNA.

EMBODIMENTS

Generally, the present disclosure is directed to the use of microRNAs (miRs) as therapeutic targets to develop effective RNA-based therapeutic interventions to diagnose and treat neurodegenerative diseases and/or psychiatric disorders. Applicant has discovered certain miRs are elevated in neurodegenerative diseases even prior to exhibiting symptomatic characteristics associated with the neurological disease. A list of early stage differentially regulated miRs is provided in Table 2. Accordingly, one aspect of the present disclosure relates to the detection of elevated miRs as a diagnostic screen for early detection of neurodegenerative diseases. More particularly, in one embodiment, miRs selected from the group consisting of miR142-3p, miR142-5p, miR181a, miR181b, miR219-3p and miR219-5p have been identified as being upregulated in the hippocampi of animal models of neurodegeneration.

In accordance with one embodiment the neuroinflammation is a result of at least one condition selected from the group of a neurodegenerative disease and a psychiatric disorder. In one embodiment the neuroinflammation is a result of a neurodegenerative disease selected from the group consisting of Alzheimer's disease, Picks disease, post-encephalitic Parkinsonism, and combinations thereof. In one embodiment the neuroinflammation is a result of a psychiatric disorder wherein the psychiatric disorder is schizophrenia.

Accordingly, in one aspect, the present disclosure is directed to methods of diagnosing a neuroinflammation, for example neuroinflammation resulting from one or more neurodegenerative disease. In particular, the present method can be used to detect neuroinflammation and the risk of developing a neurodegenerative disease prior to the patient exhibiting traits symptomatic of the neurodegenerative disease allowing for early treatment methods. The method of diagnosing neuroinflammation in a presymptomatic patient generally includes obtaining a reference expression level of one or more target miRs; and determining an expression level of the corresponding miRs in a sample obtained from the patient. An increase in the expression level of the miRs in the sample obtained from the patient as compared to the reference expression level indicates neuroinflammation, indicative of one or more neurodegenerative disease.

In one embodiment, the present disclosure relates to the use of one or more miRs selected from the group consisting of miR142-3p, miR142-5p, miR181a, miR181b, miR219-3p and miR219-5p, as biomarkers for the development of neuroinflammation and neurodegenerative diseases. In one embodiment, the present disclosure relates to the use of two or three miRs selected from the group consisting of miR142-3p, miR142-5p, miR181a, miR181b, miR219-3p and miR219-5p, as biomarkers for the development of neuroinflammation and neurodegenerative diseases. In one embodiment, the present disclosure relates to the use of two miRs selected from the group consisting of miR142-3p, miR142-

5p, miR181a, and miR181b as biomarkers for the development of neuroinflammation and neurodegenerative diseases.

A further embodiment relates to the use of an miR selected from the group consisting of miR142-3p, miR142-5p, miR181a, and miR181b, or any combination thereof, as biomarkers for the development of neuroinflammation and neurodegenerative diseases. A further embodiment relates to the use of an miR selected from the group consisting of miR142-5p and miR181b, as a biomarker for the development of neuroinflammation and neurodegenerative diseases. A further embodiment relates to the use of an miR selected from the group consisting of miR142-5p and miR181a as a biomarker for the development of neuroinflammation and neurodegenerative diseases. A further embodiment relates to the use of an miR selected from the group consisting of miR142-3p and miR181b, as a biomarker for the development of neuroinflammation and neurodegenerative diseases. A further embodiment relates to the use of an miR selected from the group consisting of miR142-3p and miR181a as a biomarker for the development of neuroinflammation and neurodegenerative diseases. A further embodiment relates to the use of an miR selected from the group consisting of miR142, as a biomarker for the development of neuroinflammation and neurodegenerative diseases. A further embodiment relates to the use of miR142-5p as a biomarker for the development of neuroinflammation and neurodegenerative diseases. A further embodiment relates to the use of miR142-3p as a biomarker for the development of neuroinflammation and neurodegenerative diseases. A further embodiment relates to the use of miR181a or miR181b as a biomarker for the development of neuroinflammation and neurodegenerative diseases.

In one embodiment a method of detecting neuroinflammation in a patient is provided wherein the expression level of an miR, selected from the group consisting of miR142-3p, miR142-5p, miR181a, miR181b, miR219-3p and miR219-5p, is determined using a biological sample recovered from the patient. The patient's biological sample can be blood, sera, plasma, cerebrospinal fluid or brain tissue. The detected levels of expression for the miR is then compared to a standardized reference expression level of the miR as found in a population of healthy patients not afflicted by a neurodegenerative disease. Patients demonstrating a threshold level of expression, and/or a significantly increased level of expression of an miR selected from the group consisting of miR142-3p, miR142-5p, miR181a, miR181b, miR219-3p and miR219-5p are designated as having neuroinflammation and an increased risk of developing a neurodegenerative disease.

In accordance with one embodiment a method of detecting neuroinflammation in a patient is provided, wherein the method comprises obtaining a reference expression level of miR142-3p, miR142-5p, miR181a, miR181b, miR219-3p and miR219-5p, determining an expression level of the corresponding miR142-3p, miR142-5p, miR181a, miR181b, miR219-3p and miR219-5p in a sample obtained from the patient, wherein an increase in the expression level of one or more of miR142-3p, miR142-5p, miR181a, miR181b, miR219-3p and miR219-5p in the sample obtained from the patient as compared to the reference expression level indicates neuroinflammation. In accordance with one embodiment the reference expression level of the miR is obtained based on population data of average miR expression levels. In an alternative embodiment, the reference expression level of the miR is calculated simultaneously with the calculation of the expression level of patient's sample expression levels using a reference sample recovered from individuals devoid of any neurodegenerative disease. In one embodiment the steps of calculating the reference expression level comprises the steps of providing a reference sample comprising RNA, wherein said reference sample is obtained from a patient free of any neurodegenerative disease. In accordance with one embodiment the expression levels of the miR are determined using real time PCR amplification. However, any technique known to those skilled in the art can be used to identify and quantitate the miR expression. For example, expression level can be quantitatively measured by methods known by those skilled in the art such as northern blotting, amplification, polymerase chain reaction, microarray analysis, tag-based technologies (e.g., serial analysis of gene expression and next generation sequencing such as whole transcriptome shotgun sequencing or RNA-Seq), Western blotting, enzyme linked immunosorbent assay (ELISA), in situ hybridization, and combinations thereof.

In accordance with one embodiment, a method of detecting neuroinflammation in a patient in a presymptomatic stage of a neurodegenerative disease is provided. The method comprises providing a test sample comprising RNA from said presymptomatic patient;

contacting the test sample with a reverse transcriptase primer specific for micro RNAs selected from the group consisting of miR142-3p, miR142-5p, miR181a, miR181b, miR219-3p and miR219-5p and reverse transcribing the micro RNA to produce a corresponding test cDNA;

contacting the test cDNA with PCR primers specific for the corresponding test cDNA that was generated from micro RNAs selected from the group consisting of miR142-3p, miR142-5p, miR181a, miR181b, miR219-3p and miR219-5p;

conducting a PCR reaction on said test cDNA, using a forward and reverse primer specific for the test cDNA and detecting the resulting amplified product;

determining the expression level of said micro RNA in said test sample based on the detected test cDNA;

obtaining a reference expression level of the corresponding micro RNA; wherein a detected higher expression level of said micro RNA in the test sample as compared to the reference expression level of said micro RNA indicates neuroinflammation. In one embodiment the method of determining miR expression levels in the test sample comprises using a reverse transcriptase primer and PCR primers specific for micro RNAs selected from the group consisting of miR142-3p, miR142-5p, miR181a, and miR181b, or any combination thereof, and the expression level of the miR(s) in the test sample is determined and compared to the reference expression level of the corresponding micro RNA. In one embodiment the method of determining miR expression levels in the test sample comprises using a reverse transcriptase primer and PCR primers specific for micro RNAs selected from the group consisting of miR142-3p, and miR142-5p or a combination of both, and the expression level of the miR(s) in the test sample is determined and compared to the reference expression level of the corresponding micro RNA. In one embodiment the method of determining miR expression levels in the test sample comprises using a reverse transcriptase primer and PCR primers specific for miR-142, and the expression level of miR-142 in the test sample is obtained. In one embodiment the method of determining miR expression levels in the test sample comprises using a reverse transcriptase primer and PCR primers specific for miR-142-3p, and the expression level of miR-142-3p in the test sample is obtained. In one embodiment the method of determining miR expression levels in the test sample comprises using a reverse transcriptase primer and PCR primers specific for miR-142-5p, and the expression level of miR-142-5p in the test sample is obtained.

In accordance with one embodiment, the steps of calculating the reference expression level comprises the steps of providing a reference sample comprising RNA, wherein said reference sample is obtained from a patient free of any neurodegenerative disease;

contacting the reference sample with a reverse transcriptase primer specific for micro RNAs selected from the group consisting of miR142-3p, miR142-5p, miR181a, miR181b, miR219-3p and miR219-5p and reverse transcribing the micro RNA to produce a corresponding reference cDNA;

conducting a PCR reaction on said reference cDNA, using a forward and reverse primer specific for the reference cDNA and detecting the resulting amplified product; and determining the expression level of said micro RNA in the reference sample based on the detected reference cDNA. In one embodiment the reference sample is contacted with PCR primers specific for micro RNAs selected from the group consisting of miR142-3p, miR142-5p, miR181a, and miR181b, or any combination thereof, and the expression level of the miR(s) are determined. In one embodiment the method of determining miR expression levels in the test sample comprises using a reverse transcriptase primer and PCR primers specific for micro RNAs selected from the group consisting of miR142-3p, miR142-5p, miR181a, and miR181b, or any combination thereof, and the expression level of the miR(s) are determined and compared to the reference expression level of the corresponding micro RNA. In one embodiment the method of determining miR reference expression levels in the reference sample comprises using a reverse transcriptase primer and PCR primers specific for micro RNAs selected from the group consisting of miR142-3p, and miR142-5p or a combination of both, and the expression level of the reference miR(s) are determined. In one embodiment the method of determining miR reference expression levels in the reference sample comprises using a reverse transcriptase primer and PCR primers specific for miR-142, and a reference expression level of miR-142 is obtained. In one embodiment the method of determining miR reference expression levels in the reference sample comprises using a reverse transcriptase primer and PCR primers specific for miR-142-3p, and a reference expression level of miR-142-3p is obtained. In one embodiment the method of determining miR reference expression levels in the reference sample comprises using a reverse transcriptase primer and PCR primers specific for miR-142-5p, and a reference expression level of miR-142-5p is obtained.

In one embodiment the expression of the micro RNA in the test sample and the reference sample are determined using a TaqMan micro RNA assay in combination with at two step RT-PCR procedure wherein, a) cDNA is first prepared by conducting a reverse transcription step on total RNA from either the test sample or the reference sample using a specific RT RNA primer; and b) PCR is conducted on the cDNA produced in step a) using a forward and reverse primer specific for the cDNA in the presence of a fluorescent labeled probe that binds to said cDNA. The fluorescent labeled probe comprises both a fluorescent emitter and quencher that produce a signal upon excitation only when the probe is hydrolyzed and the quencher and emitter are released. Only probe that specifically binds to the synthesized target template will be hydrolyzed and thus fluorescence can be monitored in real time to quantitate the amount of miR present in the original sample.

In one embodiment the method of detecting neuroinflammation further comprises the steps of detecting mRNAs that are upregulated or downregulated by miRs selected from the group consisting of miR142-3p, miR142-5p, miR181a, miR181b, miR219-3p and miR219-5p. In one embodiment the method further comprises a step of determining the expression of at least one of C1qA, C1qB, and C1qC in the test sample relative to a reference expression level.

In accordance with one embodiment a kit is provided for conducting quantitative analysis of miR levels in a sample. In one embodiment the kit comprises reverse transcriptase primers, PCR primers and/or probes specific for miRs selected from the group consisting of miR142-3p, miR142-5p, miR181a, miR181b, miR219-3p and miR219-5p. In one embodiment the kit comprises primers and probes specific for miRs selected from the group consisting of miR142-3p, miR142-5p, miR181a and miR181b. In one embodiment the kit comprises primers and probes specific for miRs selected from the group consisting of miR142-3p and miR142-5p. In further embodiment the kit may include reverse transcriptase, polymerases and buffers for conducting the assays. In one embodiment the kit may include additional reagents for detecting mRNAs that are upregulated or downregulated by miRs selected from the group consisting of miR142-3p, miR142-5p, miR181a, miR181b, miR219-3p and miR219-5p. In one embodiment the kit further comprises reagents for determining the expression of at least one of C1qA, C1qB, and C1qC.

In one embodiment a method of detecting neuroinflammation in a patient is provided wherein the method comprises obtaining a reference expression level of miR-142;

determining an expression level of miR-142 in a sample obtained from the individual, wherein an increase in the expression level of miR-142 in the sample obtained from the individual as compared to the reference expression level indicates neuroinflammation. More particularly, in one embodiment the detected miR-142 expression level represents expression levels of an miR selected from the group consisting of miR-142-3p, miR-142-5p and combinations thereof.

In one embodiment the present disclosure relates to the use of miR-142 as a biomarker for the development of neurodegenerative diseases such as dementia (e.g., Alzheimer's disease) and psychiatric diseases (e.g., schizophrenia). A microRNA screen showed that miR-142 is upregulated in the hippocampi of animal models of neurodegeneration. miR-142-5p and miR-142-3p, encoded by miR-142 pre-miR, have been shown to be upregulated in the hippocampus and plasma of a tauopathy animal model, rTg4510 mice, at the presymptomatic stage. Further, miR-142 targets several key players in the inflammatory axis, including complement proteins (C1qA, C1qB, and C1qC) that are associated with neuroinflammation and neurodegeneration. All of these complement proteins are upregulated in rTg4510 brains as well as wildtype brains that are overexpressing miR-142. These findings highlight miR-142's potential as a biomarker for neurodegenerative diseases.

Accordingly, in one aspect, the present disclosure is directed to methods of diagnosing a neuroinflammation, for example neuroinflammation resulting from one or more neurodegenerative disease. In one embodiment, a method of diagnosing neuroinflammation includes obtaining a reference expression level of miR-142; and determining an expression level of miR-142 in a sample obtained from a patient. An increase in the expression level of miR-142 in the sample obtained from the patient as compared to the reference expression level indicates neuroinflammation, indicative of one or more neurodegenerative disease.

As noted above, miR-142 targets at least complement proteins C1qA, C1qB and C1qC. Accordingly, in some embodiments, the methods further include obtaining a reference expression level of at least one complement protein selected from C1qA, C1qB, and C1qC; and determining an expression level of at least one of C1qA, C1qB, and C1qC in a sample obtained from the individual.

In another aspect, anti-miR based therapy is used to reduce neuroinflammation. Particularly, the present disclosure includes methods of reducing miR expression levels in patients identified with elevated miR expression of an miR selected from the group consisting of miR142-3p, miR142-5p, miR181a, miR181b, miR219-3p and miR219-5p. For example, in one embodiment, the methods include the use of interference RNAs or antisense oligonucleotides wherein the interference RNAs or antisense oligonucleotides are complementary to one or more miRs selected from the group consisting of miR142-3p, miR142-5p, miR181a, miR181b, miR219-3p and miR219-5p. In one embodiment, the methods include the use of interference RNAs or RNA-based antisense oligonucleotides complementary to a miR-142 (-3p and -5p) nucleotide sequence in a pharmaceutical formulation to reduce neuroinflammation. Techniques for modulation of miRNA activity by miRNA mimics and antimiR oligonucleotides are known to those skilled in the art as described in Eva van Rooij et al, EMBO Molecular Medicine (2014) e201100899. The sequence of miR142-5p is provided as SEQ ID NO: 1; the sequence of miR142-3p is provides as SEQ ID NO: 2.

In accordance with one embodiment a method of treating neuroinflammation in a patient in a presymptomatic stage of a neurodegenerative disease is provided. The method comprises the steps of administering a therapeutic that reduced the expression of a micro RNA selected from the group consisting of miR142-3p, miR142-5p, miR181a, miR181b, miR219-3p and miR219-5p, wherein one or more of the miRs have been identified as being elevated in their expression in the patient. More particularly in accordance with one embodiment the therapeutic comprises one or more antimiR oligonucleotides targeted to the miRs that have elevated expression levels relative to a reference level of expression. In one embodiment the patient is administered a pharmaceutical composition comprising antimiR oligonucleotides targeted to miR142-3p or miR142-5p or a combination thereof.

In accordance with one embodiment a method of treating individuals for neuroinflammation and/or a neurodegenerative disease comprises a first step of identifying patients that are suffering from neuroinflammation and then treating that subset of patients with antimiR oligonucleotide therapeutic formulations. In one embodiment the method comprises a first step of identifying patients suffering from neuroinflammation, said steps comprising obtaining a reference expression level of an miR selected from the group consisting of miR142-3p, miR142-5p, miR181a, miR181b, miR219-3p and miR219-5p; and determining an expression level of a corresponding miR selected from the group consisting of miR142-3p, miR142-5p, miR181a, miR181b, miR219-3p and miR219-5p in a sample obtained from the patient, wherein an increase in the expression level of said miR in the sample obtained from the patient as compared to the reference expression level indicates neuroinflammation. In one embodiment the patient is first identified as suffering from neuroinflammation by obtaining a reference expression level of an miR selected from the group consisting of miR142-3p and miR142-5p; and determining an expression level of the corresponding miR142-3p or miR142-5p in a sample obtained from the patient, wherein an increase in the expression level of said miR in the sample obtained from the patient as compared to the reference expression level indicates neuroinflammation. Once patients that are suffering from neuroinflammation have been identified, the patient is then treated by administering therapeutics that reduce the expression of the identified elevated expressed miRs. In one embodiment the expression of the identified elevated expressed miRs is reduced by administering an antisense oligonucleotide or interference RNA complementary to the detected one or more elevated miRs, selected from the group consisting of miR142-3p, miR142-5p, miR181a, miR181b, miR219-3p and miR219-5p. In one embodiment the antisense oligonucleotide or interference RNA is administered in a pharmaceutical formulation comprising one or more pharmaceutically acceptable carriers. In one embodiment the pharmaceutical composition comprises an antisense oligonucleotide or interference RNA complementary to 2 or 3 miRs selected from the group consisting of miR142-3p, miR142-5p, miR181a, miR181b, miR219-3p and miR219-5p. Alternatively in one embodiment the pharmaceutical composition comprises an antisense oligonucleotide or interference RNA complementary to an miR selected from the group consisting of miR-142-3p and miR-142-5p.

Accordingly in one embodiment a pharmaceutical composition comprising antisense oligonucleotide or interference RNA complementary to an miRs selected from the group consisting of miR142-3p, miR142-5p, miR181a, miR181b, miR219-3p and miR219-5p or a pharmaceutically acceptable salt thereof, and a pharmaceutically acceptable carrier is provided. In one embodiment the pharmaceutical composition comprises an antisense oligonucleotide or interference RNA complementary to an miRs selected from the group consisting of miR142-3p, miR142-5p, miR181a, and miR181b, and a pharmaceutically acceptable carrier. In one embodiment the pharmaceutical composition comprises an antisense oligonucleotide or interference RNA complementary to an miRs selected from the group consisting of miR142-3p and miR142-5p, and a pharmaceutically acceptable carrier.

In yet another aspect, the present disclosure is directed to the use of miR-142 based therapies to treat neurodegenerative diseases and/or psychiatric disorders. In one embodiment the method of treating comprises a first step of identifying patients having an elevated expression of an miR selected from the group consisting of miR142-3p, miR142-5p, miR181a, miR181b, miR219-3p and miR219-5p. Once patients have been identified as suffering from neuroinflammation, the patient is then treated by administering therapeutics that reduce the expression levels of the corresponding elevated miR. Particularly, the present disclosure includes methods of reducing miR-142 expression levels. For example, in one embodiment, the methods include the use of RNA-based antisense oligonucleotides or interference RNA complementary to a miR-142 (-3p and -5p) nucleotide sequence in a pharmaceutical formulation to treat these diseases. In one embodiment the antisense oligonucleotides or interference RNA is an nucleic acid mimetic to enhance the stability of the antisense oligonucleotides or interference RNA.

Suitable dosages of the antisense oligonucleotides or interference RNA for use in the methods of the present disclosure will depend upon a number of factors including, for example, age and weight of an individual, at least one precise neurodegenerative disease requiring treatment, severity of a disease, specific antisense oligonucleotide to be used, nature of a formulation, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

As noted above, the antisense oligonucleotides and interference RNA can be included in a pharmaceutical formulation. The formulation may include one or more pharmaceutically acceptable carriers, including, for example, excipients, vehicles, diluents, and combinations thereof. For example, where the formulations are to be administered orally, they may be formulated as tablets, capsules, granules, powders, or syrups; or for parenteral administration, they may be formulated as injections (intramuscular, subcutaneous, intramedullary, intrathecal, intraventricular, intravenous, intravitreal), drop infusion preparations, or suppositories. These formulations can be prepared by conventional means, and, if desired, the active compound (i.e., antisense oligonucleotide) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the pharmaceutical formulations of the present disclosure can further include additional known therapeutic agents, drugs, and the like for alleviating, mediating, preventing, and treating the diseases, disorders, and conditions described herein.

The pharmaceutical formulations including the antisense oligonucleotide, interference RNA and/or pharmaceutical carriers used in the methods of the present disclosure can be administered to a subset of individuals in need. As used herein, an "individual in need" refers to an individual at risk for or having a neurodegenerative disease, and in particular, dementia (e.g., such as tauopathy and Alzheimer's disease), Picks disease, post-encephalitic Parkinsonism, and a psychiatric disorder (e.g., schizophrenia). Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein. In particular, the individual in need is a human. The individual in need can also be, for example, a research animal such as, for example, a non-human primate, a mouse, a rat, a rabbit, a cow, a pig, and other types of research animals known to those skilled in the art.

Various functions and advantages of these and other embodiments of the present disclosure will be more fully understood from the examples shown below. The examples are intended to illustrate the benefits of the present disclosure, but do not exemplify the full scope of the disclosure.

Example 1

Identification of Altered miRs Expression in rTg4510 Mice

In this Example, miRs whose expression is significantly altered in the hippocampus and plasma of rTg4510 mice, a murine model of tauopathy, were identified. Particularly, the rTg4510 mouse line overexpresses human P301L Tau only in the forebrain, and is used as an animal model to examine miR changes resulting from forebrain Tau overexpression. rTg4510 overexpresses human tau that carries the FTDP-17 mutation (P301L) under the control of CAMKIIα-tTa. Tau mice exhibit significant neuronal loss from 3 months (m) old and robust formation of neurofibrillary tangle (NFT) pathology at 4-5 months.

RNA Deep Sequencing using Illumina platform (LC Sciences) was performed on hippocampus tissue and plasma samples at presymptomatic (2M: 3 littermate-pairs) and symptomatic (6M: 2 ctrls and 4 Tau) age. Bioinformatics analysis including differential miR expression, target analysis using Targetscan, miRanda and PITA, and pathway analysis was performed by AccuraScience. qPCR was performed using Taqman assays (Life Technologies). mRNA deep sequencing was performed on hippocampus tissue (2M: 3littermate-pairs). More particularly, the brain tissue (hippocampus) was extracted from control (tau negative, ttA negative or tau positive, ttA negative) and tau animals (tau positive, ttA positive) at different age groups: postnatal day 15, 1-month, 2-month (presymptomatic) and 6-month (postsymptomatic). Total ribonucleic acid (RNA) was extracted from the hippocampi samples using miRvana microRNA isolation kit (Life Technologies Inc.). cDNA was prepared using TaqMan® MicroRNA Reverse Transcription Kit using miR142-3p and miR142-5p specific assays (Life Technologies Inc.). U6 snRNA was used as the normalization control. Real time PCR was performed on QuantStudio™ 7 Real Time PCR machine (Applied Biosystems) using miR142-3p, miR142-5p and U6 specific assays. The mature sequence of both miR142-3p and -5p are conserved among mouse, rat and humans.

It was found that several miRs were significantly changed at presymptomatic (2-mo) and postsymptomatic stages (6-mo) of the disease progression in rTg4510 mice. Some of these miRs are common and show similar changes in their expression levels, while many are specific to the time points tested (see FIG. 1A).

A few miRs were validated using real-time PCR, namely miR-142 (-3p and -5p), miR-181 (-3p and -5p), miR219 (-3p and -5p) and miR-150 with additional time points (FIG. 1A). These miRs were common to both 2-mo and 6-mo time points. 6-month old control and rTg4510 mice were perfused with 4% paraformaldehyde and the brains were extracted. Coronal sections of brains were subjected to in-situ hybridization (ISH) with miR142-3p and U6 specific miRCURY LNA detection probes (Exiqon Inc.). The same sections were also labeled with neuronal specific (NeuN staining) and microglia specific (Iba-1 staining) specific antibodies.

Primers were designed for mouse specific complement proteins (C1QA, C1QB, C1QC) and GAPDH. cDNA was prepared from total RNA extracted form hippocampi of rTg4510 mice as described above using iscript cDNA preparation kit (Biorad). QPCR was done for complement proteins using Sybergreen master mix (Biorad). GAPDH was used as normalization control.

The primer sequences are as follows:

```
C1QA (Forward):
AGCTTTCTCAGCCATTCG          (SEQ ID NO: 3)

C1QA (Reverse Complement):
ACAAAGGTCCCACTTGGA          (SEQ ID NO: 4)
```

```
-continued
C1QB (Forward):
TCGGCCCTAAGGGTACT          (SEQ ID NO: 5)

C1QB (Reverse Complement):
TGCGTGGCTCATAGTTCT         (SEQ ID NO: 6)

C1QC (Forward):
ATTACAACCCAAGCACAGG        (SEQ ID NO: 7)

C1QC (Reverse Complement):
GACCTGCTTGCTGTTGAA         (SEQ ID NO: 8)

GAPDH (forward):
TGCACCACCAACTGCTTAGC       (SEQ ID NO: 9)
and

GAPDH (Reverse Complement):
GGCATGGACTGTGGTCATGAG.     (SEQ ID NO: 10)
```

For the primary neuronal culture, ICR strain of mice was used. Cortices of embryos at embryonic day 16.5 (E16.5) were used for primary neuronal culture. 7 days later, miR142-3p specific lentivirus (Dharmacon) was added at the titre concentration of 108 transfection units per ml. On day 12, total RNA was extracted, and complement protein was measured. MiR-142-3p showed significant induction in the hippocampus from as early as post-natal day 15 (P-15), which persisted until 6 months.

Next, the downstream transcriptomic changes that can occur with overexpression of miR-142 were assessed. Specifically, miR-142 (-5p and -3p) was overexpressed in the cortical neurons of mouse embryos at E14.5 stage of development using in-utero electroporation technique (IUE) (results shown in Tables 1 and 2). More particularly, for miR142 (-3p and -5p) overexpression the plasmid vector was purchased from Cell Biolabs, Inc (miRNASelect™ pEGP-mmu-mir-142 Expression Vector). tdTomato control vector was purchased from Addgene (pAAV-CAG-tdTomato (codon diversified)). The cortices were harvested at one-month of age.

TABLE 1

Common upregulated genes

| Common upregulated genes | Gene Names |
| --- | --- |
| Dusp4 | Dual specificity phosphatase 4 |
| Rspo2 | R-spondin 2 |
| Egr2 | Early growth response 2 |
| Glp1r | Glucagon-like peptide 1 receptor |
| Nr4a1 | Nuclear receptor subfamily 4, group A, member 1 |
| Junb | Jun B proto-oncogene |
| Nab2 | Ngfi-A binding protein 2 |
| Camk1g | Calcium/calmodulin-dependent protein kinase I gamma |
| Egr1 | Early growth response 1 |
| Egr4 | Early growth response 4 |
| Per1 | Period circadian clock 1 |
| Rtn4rl2 | Reticulon 4 receptor-like 2 |

TABLE 2

Common downregulated genes

| Common downregulated genes | Gene names |
| --- | --- |
| Ccr6 | Chemokine (C-C motif) receptor 6 |
| Lair1 | Leukocyte-associated Ig-like receptor 1 |
| Gas5 | Growth arrest specific 5 |
| Mpp7 | Membrane protein palmitoylated 7 |
| Tor3a | Torvin family 3, member A |
| Fhit | Fragile histidine triad gene |
| Sv2c | Synaptic vesicle glycoprotein 2c |
| Nexn | Naculin |
| Strip2 | Striatin interacting protein 2 |
| Sh3rf2 | SH3 domain containing ring finger 2 |
| Coch | Cochlin |
| Adora2a | Adanosine A2a receptor |
| Tcm1 | Tectonic family member 1 |
| Gpr55 | G-protein couple receptor $$ |
| Tfrc | Transferrin receptor |
| Ptgs2 | Prostaglandin-endoperoxide synthase 2 |
| Map3k14 | Mitogen-activated protein kinase kinase kinase 14 |
| Csf1 | Colony stimulating factor 1 |

Overexpression of miR-142 in brain sections revealed an increase in microglia and activated astrocytes in the proximity of miR-142 positive neurons (See FIG. 2), indicative of a phenotype characterized by inflammation. Further, total RNA was extracted and the increased levels of miR-142-3p and miR-142-5p were detected in tau mice relative to control at P-15, 1 Mo, 2 Mo and 6 Mo (see FIG. 3). Complement protein was measured relative to control at ages P-15, 1 Mo, 2 Mo and 6 Mo and the data is presented in the graphs of FIGS. 4 and 5A & 5B.

These results indicate that miR-142 partly mediates inflammation observed in the brains of tau mice.

Example 2

Analysis of RNA Changes Contributing to Tauopathy.

To investigate miR and mRNA changes at presymptomatic stage of tauopathy, miR-RNA pairing analysis was conducted to identify putative miR targets. More particularly the role of miR142, one of the identified miRs upregulated in tauopathy, was investigated to determine its impact on gene expression. In summary, miR changes at an early stage of tauopathy are anticipated to contribute to disease progression.

Methods:

Animals

The generation and genotyping of rTg(TauP301L)4510 (rTg4510) mice were conducted as previously described. rTg4510 mice over-express the P301L mutation in 4R0N human Tau associated with FTDP-17. To minimize this effect of heterogeneous phenotype due to genetic background, littermate controls were used for all the experiments. All mice were housed in standard conditions with food and water provided ad libitum and maintained on a 12 hr dark/light cycle.

RNA Sequencing and Pathway Analysis

Small RNA sequencing was performed by LC Sciences (Houston, Tex., USA). The quantity and purity of total RNAs were assessed using a NanoDrop ND-1000 spectrophotometer (NanoDrop Inc., Wilmington, Del., USA) at a 260/280 ratio 2.0. The integrity of total RNAs was analyzed using an Agilent 2100 Bioanalyzer system and RNA 6000 Nano LabChip Kit (Agilent Tech, Santa Clara, Calif., USA) with RNA integrity number greater than 7.0. The libraries were constructed from total RNA using the Illumina Truseq Small RNA Sample Preparation Protocol #15004197 Rev. F (Catalog #RS-200-9002DOC; Illumina, San Diego, Calif., USA) according to the manufacturer's protocol. Briefly, RNA adapters were ligated to target miRNAs in two separate steps. Reverse transcription reaction was applied to the ligation products to create single stranded cDNA. The cDNA was amplified by PCR using a common primer and a primer containing the index sequence, and subsequently purified by PAGE-gel. Before sequencing, libraries were qualified on the Bioanalyzer High Sensitivity DNA Chip. Finally, Illumina sequencing technology was employed to sequence these prepared libraries. The raw sequences were generated using the Illumina HiSeq 2500 platform (50 bp SE, rapid-run mode). After masking of the adaptor sequences and removal of contaminated reads, the clean reads were filtered and analyzed for miRNA prediction with the software package ACGT101-miR-v4.2 (LC Sciences, Houston, Tex., USA). The data discussed here have been deposited in NCBI's Gene Expression Omnibus and are accessible through GEO Series accession number GSE106967.

Standard data analysis was performed on the deep sequencing by using a proprietary pipeline script, ACGT101-miR v4.2 (LC Sciences Inc.). For 2 m hippocampi, miRNA seq yielded 74,720,901 raw sequences. Of these, the total mappable sequences were 64,833,130. 67.8% (43,975,586 reads) reads mapped to the mouse miRs annotated in miRBase repository, a comprehensive database for miR sequence data (Nucleic Acids Res 34, D140-144 (2006). The mappable reads to known mouse miRs corresponded to 1,690 miRs. The majority of sequences were in the range of 18-23 nucleotides, consistent with the reported length of metazoan miRs. For 6 m hippocampi, sequencing of small RNA yielded 71,431,722 raw sequences. Among these, there were 64,337,423 mappable reads. The mappable reads to known miRs correspond to 1,743 mouse miRs. mRNA sequencing was performed by Center for Medical Genomics, Indiana University School of Medicine.

1. Library Preparation and Sequencing:

The concentration and quality of total RNA samples was first assessed using Agilent 2100 Bioanalyzer. A RIN (RNA Integrity Number) of five or higher was required to pass the quality control. Then five hundred nanograms of RNA per sample were used to prepared single-indexed strand-specific cDNA library using TruSeq RNA Access Library Prep Kit (Illumina). The resulting libraries were assessed for its quantity and size distribution using Qubit and Agilent 2100 Bioanalyzer. One and a half pico molar pooled libraries were sequenced with 1.75 bp single-end configuration on NextSeq500 (Illumina) using NextSeq 500/550 High Output Kit. A Phred quality score (Q score) was used to measure the quality of sequencing. More than 90% of the sequencing reads reached Q30 (99.9% base call accuracy).

2. Sequence Alignment and Gene Counts:

The sequencing data were first assessed using FastQC (Babraham Bioinformatics, Cambridge, UK) for quality control. Then all sequenced libraries were mapped to the mouse genome (UCSC mm10) using STAR RNA-seq aligner with the following parameter: "--outSAMmapqUnique 60". The reads distribution across the genome was assessed using bamutils (from ngsutils). Uniquely mapped sequencing reads were assigned to mm10 annotated genes using featureCounts (from subread) with the following parameters: "-s 2 -Q 10". Quality control of sequencing and mapping results was summarized using MultiQC. Genes with read count per million (CPM) >0.5 in more than 3 of the samples were retained. The data was normalized using TMM (trimmed mean of M values) method. Differential expression analysis was performed using edgeR. False discovery rate (FDR) was computed from p-values using the Benjamini-Hochberg procedure. The mRNA-seq data discussed here have been deposited in NCBI's Gene Expression Omnibus and are accessible through GEO Series accession numbers: GSE107183, GSE107167.

The multi-dimensional scaling (MDS) plot of the RNA samples was drawn using plotMDS function in edgeR. The distance represented the leading log-fold-changes between each pair of RNA samples, which is the average (root-mean-square) of the largest absolute log-fold changes between each pair. This visualizes the differences between the expression profiles of different samples in two dimensions. Pathway analysis: Ingenuity Pathway Analysis (IPA, Qiagen, Germantown, Md.) was performed for differentially expressed genes with FDR <0.05. Enrichment of Canonical Pathways and Disease and Bio Functions were identified with threshold $p<0.05$. The activity of pathways and functions was inferred as z-scores. Positive z-score indicated increased activity, while negative z-score indicated inhibited activity.

The miRNA target filter in Qiagen's IPA software was used for pairing of the miRNA-seq and mRNA-seq data sets. Differentially expressed miRNAs ($P<0.05$) were uploaded into IPA and analyzed with the miRNA target filter, which includes experimentally validated and predicted mRNA targets from TargetScan, TarBase, miRecords and the Ingenuity Knowledge Base. Differentially expressed mRNAs (FDR<0.05) were then uploaded with the "add/replace mRNA data set" function. Using the "expression-pairing" feature, only potential targets differentially expressed in the mRNA-seq data are maintained; all other potential targets are filtered out. These target genes were than subjected to pathway analysis.

In Utero Electroporation (IUE) Procedure

Pregnant ICR female mice 14.5 d postgestation were anesthetized by isoflurane inhalation, and a small incision was made in the abdominal wall to expose the uterine horns. For miR142-OE overexpression experiment, a DNA mixture of pCAG-mGFP (membrane targeted green fluorescent protein [GFP], and miRNASelect™ pEGP-mmu-mir-142 Expression Vector (Cell Biolabs) mixed in equal amounts (1 ug/ul each), with a final concentration of 1 µg/µl each) into the left hemisphere of ~50% of the ICR embryos. The remaining embryos received only tdTomato (pAAV-CAG-tdTomato (codon diversified) (Addgene plasmid #59462), 1 µg/µL) to serve as littermate controls. Approximately 0.5-1 µL of DNA solution was injected into the lateral ventricle of embryos (E14.5) using a pulled glass micropipette. Each embryo within the uterus was placed between platinum tweezer-type electrodes (5 mm diameter, Harvard Apparatus, Inc., Holliston, Mass., USA). Square electric pulses (33-35 V, 50 ms duration, five times) were passed at is intervals using a platinum, 3-mm-diameter tweezer-type electrodes (Harvard Apparatus, Holliston, Mass.) using a BTX ECM 830 square Electroporator (Harvard Apparatus). The wall of the abdominal cavity and skin were then sutured, and the animals were allowed to develop to term and aged to 1 m. At 1 m old, control and miR142-OE mice were deeply anesthetized and decapitated to harvest brains, For RNAseq analysis, GFP- (miR142-OE) or tdTomato-positive (control) cortical tissues were dissected out from IUE mouse brains.

Gene Expression and miR Assessment

Total RNA was purified from cortex and hippocampus using the miRVana RNA isolation kit according to the manufacturer's instruction (part no. AM1560, ThermoFisher scientific, Grand Island, N.Y.). One microgram of total RNA was reverse transcribed to cDNA using the iScript™ Advanced cDNA Synthesis Kit (#1725038, Bio-Rad, Hercules, Calif.). Quantitative real-time reverse transcriptase-polymerase chain reaction (QRT-PCR) was performed using PowerUp™ SYBR™ Green Master Mix (part no. A25742, ThermoFisher scientific). The PCR reaction was run in a Quant Studio 7 Flex Real Time PCR system (Applied Biosystems, Grand Island, N.Y.). The gene expression was assessed using gene-specific primers. Gapdh was used as a reference control for normalization. The primer sequences were as follows: 1) mouse C4B: Forward 5'-GAA ATG TTA ACT TCC AGA AGG C-3' (SEQ ID NO: 11); Reverse 5'-CGT CTT CAT CTA TCA AGT CTT CC-3' (SEQ ID NO: 12) mouse TREM2: Forward 5'-CAC CAT CAC TCT GAA GAA CC-3' (SEQ ID NO: 13); Reverse 5'-AAG GAG GTC TCT TGA TTC CTT-3' (SEQ ID NO: 14); 3) mouse-Prnp: Forward 5'-TAC CCT AAC CAA GTG TAC TAC AGG-3' (SEQ ID NO: 15); Reverse 5'-GCT GGA TCT TCT CCC GT-3' (SEQ ID NO: 16); 4) mouse GFAP: Forward 5'-AAA ACC GCA TCA CCA TTC CT-3 (SEQ ID NO: 17)'; Reverse 5'-GGC AGG GCT CCA TTT TCA ATC-3 (SEQ ID NO: 18'; 5) mouse CSF1: Forward 5'-ACC CTC AGA CAT TGG ATT CT-3' (SEQ ID NO: 19); Reverse 5'-AAG CTG CTT CTT TCA TCC A-3' (SEQ ID NO: 20); 6) mouse Gapdh: Forward 5'-TGC ACC ACC AAC TGC TTA GC-3' (SEQ ID NO: 9); Reverse 5'-GGC ATG GAC TGT GGT CAT GAG-3' (SEQ ID NO: 10).

The levels of gene expression in each sample were determined with the comparative Ct method using Quant Studio 7 Flex Real Time PCR software. For gene expression, cycling parameters were as follows: 2 min at 50° C., 2 min at 95° C., 40 cycles: 15 sec at 95° C., and 1 min at 60° C. For miR studies, total RNA was isolated using the mirVana miRNA Isolation Kit, according to the manufacturer's instructions. For miR quantification by QRT-PCR, 10 ng of total RNA were used to prepare cDNA using TaqMan MicroRNA Reverse Transcription Kit (part no. 4366596, Life Technologies) and TaqMan specific probes as follows: miR142-3p (#4427975; assay ID: 000464); miR142-5p (#4427975; assay ID: 002248); miR181b (#4427975; assay ID: 465209_mat); miR181a (#4427975; assay ID: 000516); miR219-3p (#4427975; assay ID: 002390); miR219-5p (#4427975; assay ID: 000522); miR339-5p (#4427975; assay ID: 002257); miR1249 (#4427975; assay ID: 002868); U6 small nucleolar RNA (#4427975; assay ID: 001973). U6 was used as a reference control for normalization. Real-Time RT-PCR was performed using TaqMan Universal PCR Master Mix, No AmpErase UNG (#4324018, Life Technologies). The QRT-PCR cycling parameters were 2 min at 50° C., 10 min at 95° C., 40 cycles: 15 s at 95° C., and 1 min at 60° C. Data were analyzed using Quant Studio 7 Flex Real Time PCR system software (Applied Biosystems, Foster City, Calif.).

Immunofluorescence Staining and Image Acquisitions

At 1 m old, control and miR142-OE mice manipulated via IUE were deeply anesthetized by isoflurane inhalation, transcardially perfused with PBS, followed by 4% Paraformaldehyde (PFA) solution in PBS, after which the brains were removed and postfixed overnight in 4% PFA at 4°. The brains were serially sectioned in the coronal plane into 100 μm thick sections using a Leica VT-1000 vibrating microtome (Leica Microsystems, Bannockburn, Ill.). Brain slices containing comparative morphology were selected for immunofluorescence staining. For immunofluorescence staining, brain slices were washed with PBS/0.01% Triton X-100 (PBST) and permeabilized with 0.3% Triton X-100 in PBS at room temperature for 20 min. Next, blocking was performed for 1 h using 3% normal goat serum in PBST. Following this step, the cells were stained with various primary antibodies diluted in 3% normal goat serum/0.2% Triton X-100 in PBS at 4° C. overnight. The next day, cells were washed with PBST, and incubated with secondary antibodies (goat-anti rabbit/mouse/chicken IgG conjugated with Alexa 647/555/488 (1:1000 dilution in 0.2% Triton X-100 in PBS) was used to detect primary antibody at room temperature for 1 hour. Following this incubation, sections were washed with PBST three times for 10 min each, mounted in Vectashield mounting media with DAPI (Vector Labs, Burlingame, Calif.) and cover slipped for imaging. The primary antibodies used were: IBA1 (anti rabbit, 1:500, WAKO 019-19741, Richmond, Va.); GFAP (anti rabbit, 1:500, DAKO Z0334, Santa Clara, Calif.); NeuN (anti mouse, 1:500, Millipore MAB377, Burlington, Mass.); S100B (anti mouse, 1:500, Sigma AMAb91038, St. Louis, Mo.); GFP (anti chicken, 1:500, Ayes Labs Inc GFP-1020, Tigard, Oreg.).

Z stack images were obtained using Leica DFC365FX Microsystems Confocal microscope with 10×/0.30 objective. The Z-stacks were taken with 1 μm step between individual planes. All images were processed in Adobe Photoshop for brightness/contrast, orientation and background correction to better illustrate staining patterns.

Dual In Situ Hybridization and Immunostaining:

DIG-label in situ hybridization and immunostaining was performed on floating brain sections. The animals were deeply anesthetized by isoflurane inhalation, and transcardially perfused with freshly prepared 4% Paraformaldehyde (PFA, catalog no #P6148, Sigma Aldrich, MO, USA). Day 1: 60 μM sections were cut on Leica VT-1000 vibrating microtome (Leica Microsystems, Bannockburn, Ill.) and treated with proteinase K solution (Catalog no #3115887001, Roche, Indianapolis, Ind.) for 30 min at 37° C. To reduce non-specific binding, acetylation step was performed by incubating the sections with acetylation solution (0.5% acetic anhydre (Sigma Aldrich), 1.35% triethanolamine (pH 8, Sigma Aldrich), 0.067% HCl (Fluka Chemika, Buchs, Switzerland) in 0.1% DEPC-treated water (Sigma Aldrich). Probes (miRCURY LNA detection control probe U6, catalog no #99002-15, Exiqon, Germantown, Md.; miRCURY LNA detection probe hsa-miR-142-5p, catalog no #38514-15, Exiqon, Germantown, Md.) at a final concentration of 30 nM were diluted in hybridization buffer (Formamide, SSC, Yeast RNA, Heparin, Denhardts solution, Tween, EDTA) and heat-denatured at 90° C. for 2 minutes after which it was cooled on ice. Sections were incubated O/N at 55° C. with the probes (300 μL) in a wet chamber humidified with 50% Formamide-5×SSC (sodium chloride, sodium citrate) solution. Day 2: Multiple washes were performed with 5×SSC solution, followed by blocking for 1 h at RT with blocking solution (0.1% BSA, 1×PBS, 0.1% Tween). Next, sections were incubated with antibodies against DIG (Anti-Digoxigenin-AP, Fab fragments; Catalog no #11093274910, Roche, Indianapolis, Ind.), NeuN and IBA1 (1:500 dilution) for 2 nights at 4° C. Day 3: Multiple washes with 1×PBS and 1×PBS+0.3% Tween were performed at RT. Sections were incubated with appropriate fluorescent secondary antibodies (1:500 dilution) at RT for 2 hours. Sections were washed with 0.1M Tris 8.2 for 10 min and developed at RT till a red precipitate started to appear. The color reaction was stopped with 1×PBS+0.3% Tween and sections were transferred to 1M Phosphate buffer (3×5 min.) after which they were incubated for 10 minutes in 1 μg/ml Hoechst (Invitrogen, Grand Island, N.Y.) in 1M PB.

After rinsing in PB (2×5 min) sections were mounted with prolong gold mounting media for imaging.

Primary Neuronal Culture and Lentivirus Transduction

ICR pregnant females were deeply anesthetized by isoflurane inhalation, and a small incision was made in the abdominal wall to harvest their embryos for brains. Cortical tissue from E16.5 ICR embryonic brains was isolated and dissociated to acquire cortical neurons using the Worthington Papain Dissociation kit according to manufacturer's protocol (Worthington Inc.). Cortices from several embryonic brains were pooled for plating. Neurons were plated at 100,000 cells per well of a 6-well plate. Cultures were maintained in a regularly replaced Neurobasal media (Invitrogen, Grand Island, N.Y.) with B27 supplement (Invitrogen), penicillin-streptomycin supplement (Life Technologies) and L-glutamine (Invitrogen). Neurons were incubated at 37° C. and 5% humidity. On $7^{th}$ day-in-vitro (DIV7), control (VSM5954, Dharmacon; GE Healthcare) and MiR142-3p-OE (VSM6215-213652311, Dharmacon, Lafayette, Colo.) lentiviruses were added at the titer concentration of $10^{\wedge 8}$ transfection units/ml. On DIV11, total RNA was extracted using miRVana RNA isolation kit. Two independent experiments were performed from two different pregnant females and each experiment was conducted with three replicates.

Data and Statistical Analysis

Data were analyzed using GraphPad Prism 7.0 software (GraphPad Software, San Diego, Calif., USA). Means were compared across groups with the use of t tests for 2 groups for data that followed the normal distribution. Normality was assessed with the Kolmogorov-Smirnov test and significant P values were denoted by *. When the data did not follow the normal distribution, P values were computed with nonparametric Mann-Whitney methods, and significant p values were denoted by #. Two-tailed P values<0.05 were considered significant. Values are presented as means±SEM.

Results

Age-Dependent miR Expression Changes in Tau Hippocampi

The rTg4510 mouse line (abbreviated as Tau mice for simplicity) has been widely used and characterized as a tauopathy mouse model. These mice overexpress human Tau that carries the P301L mutation identified in frontotemporal dementia with Parkinsonism on chromosome 17 (FTDP-17) under the control of CAMKIIα-tTA. Forebrain-Tau(P301L) expression starts after birth and peaks at around 2 months (2 m) of age. Signs of neurodegeneration become detectable at 2.5 m. Tau tangles are observed in the cortex after 4 m and in the hippocampus after 5.5 m accompanied with severe age dependent cognitive decline and neuronal loss. To determine whether Tau(P301L) overexpression alters miR levels, we employed RNAseq (Illumina GAIIx platform with raw reads of 40 nucleotides) to assess miR changes at two time points: An early presymptomatic age when no obvious abnormalities are detected (2 m) (control, n=3; Tau, n=3); and a late symptomatic stage when severe Tau pathology and neuronal loss are evident (6 m) (control, n=2; Tau, n=4).

Differential expression analysis for known miRs between control and Tau hippocampi shows that: 121 miRs are significantly changed at 2 m (P<0.05) with 51 upregulated and 70 downregulated in Tau hippocampi; 92 miRs are significantly changed (P<0.05) at 6 m with 48 upregulated and 44 downregulated in Tau hippocampi. Among these miR changes, 21 miRs are altered in the same direction for both 2 m and 6 m (13 upregulated and 8 downregulated; a complete list of the differentially expressed annotated miRs is provided in Tables 1 and 2).

TABLE 3

Differentially regulated microRNAs at 2 months

| # | Accession ID | miR Name | Ctrl-reads (mean) | Tau-reads (mean) | p-value |
|---|---|---|---|---|---|
| Reads greater than or equal to average reads (7059) ||||||
| 1 | MIMAT0000590 | mmu-miR-342-3p | 17222.9250 | 10925.3850 | 0.0030 |
| 2 | MIMAT0000383 | mmu-let-7d-5p | 61842.8080 | 47847.7240 | 0.0070 |
| 3 | MIMAT0000163 | mmu-miR-153-3p | 16263.8970 | 7721.4640 | 0.0110 |
| 4 | MIMAT0000133 | mmu-miR-101a-3p_R + 1_1ss21AC | 13774.8440 | 22129.2610 | 0.0130 |
| 5 | MIMAT0003127 | mmu-miR-484 | 14264.9740 | 9327.4350 | 0.0140 |
| 6 | MIMAT0000673 | mmu-miR-181b-5p | 7049.9250 | 11664.6270 | 0.0140 |
| 7 | MIMAT0000137 | mmu-miR-126a-5p | 14978.4730 | 21055.9010 | 0.0140 |
| 8 | MIMAT0003151 | mmu-miR-378a-3p_R + 1 | 12119.2510 | 8760.6190 | 0.0190 |
| 9 | MIMAT0000248 | mmu-miR-30e-5p_R + 2 | 118424.9560 | 157705.2710 | 0.0200 |
| 10 | MIMAT0004746 | mmu-miR-409-5p | 21452.2360 | 9797.0180 | 0.0240 |
| 11 | MIMAT0000674 | mmu-miR-181c-5p | 7346.0270 | 9209.5900 | 0.0300 |
| 12 | MIMAT0000125 | mmu-miR-23b-3p_R + 3 | 6219.5360 | 11582.2720 | 0.0300 |
| 13 | MIMAT0000210 | mmu-miR-181a-5p | 40005.2330 | 76645.8140 | 0.0300 |
| 14 | MIMAT0000537 | mmu-miR-27a-3p | 10046.1920 | 15952.9280 | 0.0380 |
| 15 | MIMAT0000677 | mmu-miR-7a-5p_R + 1 | 19582.2740 | 7051.2790 | 0.0410 |
| 16 | MIMAT0000534 | mmu-miR-26b-5p_R + 1 | 22185.9100 | 26712.9250 | 0.0420 |
| 17 | MIMAT0000159 | mmu-miR-149-5p | 8732.0630 | 6628.4330 | 0.0430 |
| 18 | MIMAT0000138 | mmu-miR-126a-3p_R − 1 | 39121.6730 | 50870.8800 | 0.0440 |
| 19 | MIMAT0000515 | mmu-miR-30d-5p_R − 2 | 98229.8670 | 129900.8150 | 0.0440 |
| 20 | MIMAT0000546 | mmu-miR-103-3p | 14693.1980 | 11201.2170 | 0.0450 |
| 21 | MIMAT0000678 | mmu-miR-7b-5p_R + 1 | 10355.1020 | 5403.6650 | 0.0480 |
| 22 | MIMAT0022841 | mmu-miR-219a-2-3p | 5110.6020 | 10046.7080 | 0.0490 |
| Reads less than average reads (7059) ||||||
| 1 | MIMAT0000571 | mmu-miR-331-3p_R + 1 | 1880.3688 | 1677.8590 | 0.0002 |
| 2 | MIMAT0004624 | mmu-miR-15a-3p_1ss22AT | 64.5124 | 106.6957 | 0.0003 |
| 3 | MIMAT0014808 | mmu-miR-344d-3p | 426.8822 | 247.6720 | 0.0009 |
| 4 | MIMAT0019349 | mmu-miR-101c_L + 1R + 2 | 1001.2743 | 1763.5193 | 0.0023 |
| 5 | MIMAT0004826 | mmu-miR-146b-3p | 38.6537 | 57.6857 | 0.0040 |
| 6 | MIMAT0017018 | mmu-miR-16-2-3p_R − 1 | 26.3185 | 42.4596 | 0.0042 |

TABLE 3-continued

Differentially regulated microRNAs at 2 months

| # | Accession ID | miR Name | Ctrl-reads (mean) | Tau-reads (mean) | p-value |
|---|---|---|---|---|---|
| 7 | MIMAT0016997 | mmu-miR-187-5p | 270.8221 | 59.9853 | 0.0043 |
| 8 | MIMAT0005291 | mmu-miR-582-5p | 1897.3794 | 3285.7356 | 0.0044 |
| 9 | MIMAT0017040 | mmu-miR-350-5p_R + 2 | 42.6725 | 95.2445 | 0.0049 |
| 10 | MIMAT0005292 | mmu-miR-582-3p_L-1R + 2 | 776.1475 | 1397.9157 | 0.0058 |
| 11 | MIMAT0003730 | mmu-miR-592-5p_L − 1 | 458.5517 | 686.8648 | 0.0059 |
| 12 | MIMAT0014823 | mmu-miR-3057-3p | 21.5805 | 11.6656 | 0.0064 |
| 13 | MIMAT0006942 | oan-miR-103-3p_R + 1 | 59.5052 | 38.6641 | 0.0066 |
| 14 | MIMAT0017068 | mmu-miR-181c-3p | 1132.1045 | 1571.3509 | 0.0070 |
| 15 | MIMAT0001094 | mmu-miR-412-3p_L + 1 | 58.4771 | 32.4741 | 0.0079 |
| 16 | MIMAT0003735 | mmu-miR-672-5p | 572.7475 | 320.9741 | 0.0081 |
| 17 | MIMAT0003711 | mmu-miR-652-3p_R + 1 | 5872.0751 | 2566.8260 | 0.0102 |
| 18 | MIMAT0004684 | mmu-miR-362-3p__1ss22AT | 272.8543 | 337.9687 | 0.0102 |
| 19 | MIMAT0003507 | mmu-miR-500-3p_R − 1 | 387.9997 | 297.3728 | 0.0110 |
| 20 | MIMAT0000216 | mmu-miR-187-3p_R + 1 | 3112.5654 | 683.4170 | 0.0113 |
| 21 | MIMAT0017209 | mmu-miR-541-3p | 317.3998 | 100.0163 | 0.0122 |
| 22 | MIMAT0000209 | mmu-miR-129-5p | 2494.5915 | 2094.7373 | 0.0124 |
| 23 | MIMAT0000711 | mmu-miR-365-3p | 1577.8789 | 994.9661 | 0.0126 |
| 24 | MIMAT0000152 | mmu-miR-140-3p_L − 1R + 2 | 4802.0084 | 5788.5101 | 0.0127 |
| 25 | MIMAT0005792 | hsa-miR-320b__2ss20CA22AT | 47.0132 | 27.9594 | 0.0136 |
| 26 | MIMAT0003898 | mmu-miR-760-3p_R + 2 | 747.3670 | 331.1073 | 0.0139 |
| 27 | MIMAT0019339 | mmu-miR-28c_L + 1 | 359.5167 | 269.7986 | 0.0139 |
| 28 | MIMAT0010560 | mmu-miR-1249-3p | 1133.8087 | 1931.7656 | 0.0141 |
| 29 | MIMAT0005859 | mmu-miR-1198-5p | 754.4421 | 550.4306 | 0.0142 |
| 30 | MIMAT0000666 | mmu-miR-320-3p | 3914.0798 | 2634.4592 | 0.0161 |
| 31 | MIMAT0027807 | mmu-miR-6953-3p_R − 1 | 13.2084 | 7.2927 | 0.0165 |
| 32 | MIMAT0003894 | mmu-miR-764-5p_R + 3 | 46.7483 | 17.3068 | 0.0167 |
| 33 | MIMAT0036137 | chi-miR-326-5p_1ss5GA | 25.4076 | 43.8821 | 0.0170 |
| 34 | MIMAT0017017 | mmu-let-7f-2-3p_R + 1 | 230.4440 | 291.2281 | 0.0178 |
| 35 | MIMAT0035718 | mmu-miR-935_L − 2 | 162.3808 | 127.1211 | 0.0185 |
| 36 | MIMAT0025585 | mmu-miR-6540-5p_R − 1 | 438.9607 | 273.1388 | 0.0187 |
| 37 | MIMAT0016992 | mmu-miR-153-5p_L + 5 | 576.2505 | 366.5502 | 0.0188 |
| 38 | MIMAT0000584 | mmu-miR-339-5p_R − 2_1ss21AT | 383.3649 | 517.9357 | 0.0188 |
| 39 | MIMAT0014926 | mmu-miR-344b-3p | 567.2167 | 276.0596 | 0.0192 |
| 40 | MIMAT0004528 | mmu-miR-125a-3p_R − 1 | 374.1257 | 262.7612 | 0.0195 |
| 41 | MIMAT0003490 | mmu-miR-700-3p | 202.7094 | 125.7502 | 0.0196 |
| 42 | MIMAT0000532 | mmu-miR-23a-3p | 3139.2190 | 5254.2089 | 0.0201 |
| 43 | MIMAT0000233 | mmu-miR-200b-3p | 4202.5302 | 230.5671 | 0.0201 |
| 44 | MIMAT0005851 | mmu-miR-1193-3p | 713.8030 | 433.9682 | 0.0205 |
| 45 | MIMAT0000664 | mmu-miR-219a-5p | 1745.0204 | 3593.1071 | 0.0205 |
| 46 | MIMAT0017070 | mmu-miR-7a-2-3p | 204.9704 | 86.4919 | 0.0209 |
| 47 | MIMAT0014810 | mmu-miR-1298-3p | 1099.4219 | 424.2450 | 0.0210 |
| 48 | MIMAT0024360 | ppy-miR-378d_R + 3 | 139.3350 | 74.4526 | 0.0211 |
| 49 | MIMAT0000597 | mmu-miR-346-5p | 6759.8102 | 1540.1083 | 0.0212 |
| 50 | MIMAT0014934 | mmu-miR-3102-5p.2-5p_R − 1 | 59.8325 | 27.0112 | 0.0213 |
| 51 | MIMAT0004529 | mmu-miR-125b-2-3p_R − 1 | 4077.9593 | 5641.1494 | 0.0219 |
| 52 | MIMAT0000660 | mmu-miR-181a-1-3p | 1343.2453 | 2708.9901 | 0.0219 |
| 53 | MIMAT0004120 | mdo-miR-187-3p_R + 1 | 43.0333 | 10.1009 | 0.0225 |
| 54 | MIMAT0014803 | mmu-miR-1264-3p | 2957.6974 | 587.0522 | 0.0226 |
| 55 | MIMAT0004653 | mmu-miR-342-5p_R − 1 | 443.7011 | 316.8661 | 0.0234 |
| 56 | MIMAT0014802 | mmu-miR-1264-5p | 259.9885 | 86.5706 | 0.0238 |
| 57 | MIMAT0014877 | mmu-miR-3084-3p | 27.3678 | 44.0977 | 0.0246 |
| 58 | MIMAT0003780 | mmu-miR-490-3p_R + 1 | 1603.9012 | 2775.1617 | 0.0253 |
| 59 | MIMAT0006835 | oan-miR-181b-5p_R + 7 | 27.9923 | 35.7060 | 0.0254 |
| 60 | MIMAT0003167 | mmu-miR-540-3p_R + 2 | 515.7789 | 449.2134 | 0.0258 |
| 61 | MIMAT0014928 | mmu-miR-344c-3p | 121.3344 | 56.6446 | 0.0260 |
| 62 | MIMAT0004621 | mmu-let-7b-3p_1ss22CT | 818.7214 | 1038.1058 | 0.0262 |
| 63 | | PC-5p-35674_14 | 7.5830 | 2.4778 | 0.0274 |
| 64 | MIMAT0004889 | mmu-miR-504-5p | 128.7450 | 93.1411 | 0.0274 |
| 65 | MIMAT0000593 | mmu-miR-344-3p | 866.3791 | 431.4883 | 0.0275 |
| 66 | MIMAT0000236 | mmu-miR-203-3p_L − 1R + 1 | 519.5805 | 946.8774 | 0.0278 |
| 67 | MIMAT0004662 | mmu-miR-139-3p_R + 1 | 1749.5880 | 872.5954 | 0.0279 |
| 68 | MIMAT0000154 | mmu-miR-142a-5p_L + 2R − 3 | 2607.2628 | 3985.0584 | 0.0284 |
| 69 | MIMAT0004821 | mmu-miR-671-3p | 618.7329 | 1008.5249 | 0.0289 |
| 70 | MIMAT0017328 | mmu-miR-1188-3p_R − 2 | 10.5112 | 3.4010 | 0.0307 |
| 71 | MIMAT0025123 | mmu-let-7j_R − 1_1ss8TG | 4463.6111 | 3500.0757 | 0.0309 |
| 72 | MIMAT0017075 | mmu-miR-361-3p_L − 1 | 1440.5507 | 1775.9864 | 0.0311 |
| 73 | MIMAT0005440 | mmu-miR-24-2-5p | 1586.8049 | 2700.3089 | 0.0321 |
| 74 | MIMAT0009457 | mmu-miR-1839-3p_R − 2 | 270.6956 | 380.3431 | 0.0332 |
| 75 | MIMAT0017060 | mmu-miR-221-5p | 2599.4072 | 1688.9570 | 0.0339 |
| 76 | | mmu-mir-149-p3 | 7.5971 | 15.3336 | 0.0341 |
| 77 | MIMAT0001537 | mmu-miR-429-3p | 1058.8594 | 87.7023 | 0.0345 |
| 78 | MIMAT0000706 | mmu-miR-362-5p | 707.6584 | 281.3269 | 0.0348 |
| 79 | MIMAT0000540 | mmu-miR-93-5p_R − 2 | 1263.0649 | 1792.8912 | 0.0351 |
| 80 | MIMAT0000526 | mmu-miR-15a-5p_R − 1 | 664.8703 | 1027.6883 | 0.0353 |
| 81 | MIMAT0016916 | hsa-miR-4286_R + 1 | 5.7932 | 11.6903 | 0.0354 |

TABLE 3-continued

Differentially regulated microRNAs at 2 months

| # | Accession ID | miR Name | Ctrl-reads (mean) | Tau-reads (mean) | p-value |
|---|---|---|---|---|---|
| 82 | MIMAT0004629 | mmu-miR-22-5p_R − 1 | 341.1291 | 502.3946 | 0.0371 |
| 83 | MIMAT0003509 | mmu-miR-501-3p_R + 1 | 1801.6016 | 766.7501 | 0.0388 |
| 84 | MIMAT0000155 | mmu-miR-142a-3p_R − 1 | 124.0647 | 194.0203 | 0.0392 |
| 85 | MIMAT0004644 | mmu-miR-337-5p | 2690.6416 | 2158.3830 | 0.0408 |
| 86 | MIMAT0022370 | mmu-miR-5621-3p | 74.2179 | 43.9856 | 0.0414 |
| 87 | MIMAT0003734 | mmu-miR-667-3p | 2029.4411 | 1421.8106 | 0.0420 |
| 88 | MIMAT0014944 | mmu-miR-486b-3p_R + 1 | 25.9110 | 15.3719 | 0.0421 |
| 89 | MIMAT0004656 | mmu-miR-345-3p_L + 1R − 1_1ss22AT | 483.7142 | 328.6830 | 0.0432 |
| 90 | MIMAT0022384 | mmu-miR-344h-3p | 8.4994 | 2.8570 | 0.0438 |
| 91 | MIMAT0023746 | cgr-miR-1260_R + 3 | 102.8034 | 174.8222 | 0.0446 |
| 92 | MIMAT0000612 | mmu-miR-135b-5p | 514.4915 | 293.0913 | 0.0451 |
| 93 | MIMAT0000519 | mmu-miR-200a-3p | 6293.9471 | 442.8763 | 0.0458 |
| 94 | MIMAT0017069 | mmu-miR-128-2-5p | 334.8365 | 191.1010 | 0.0467 |
| 95 | MIMAT0017282 | mmu-miR-544-5p | 957.8717 | 623.3711 | 0.0480 |
| 96 | MIMAT0017067 | mmu-miR-181b-1-3p_R + 2 | 69.8928 | 133.0907 | 0.0484 |
| 97 | MIMAT0000160 | mmu-miR-150-5p | 4439.6832 | 6448.1987 | 0.0485 |
| 98 | MIMAT0004820 | mmu-miR-744-3p | 155.2825 | 262.7418 | 0.0486 |

TABLE 4

Differentially regulated microRNAs at 6 months

| # | Accession ID | Name | Ctrl-reads (mean) | Tau-reads (mean) | p-value |
|---|---|---|---|---|---|
| | Reads greater than or equal to average reads (7616) | | | | |
| 1 | mmu-miR-221-3p | MIMAT0000669 | 20697.0118 | 7951.0457 | 0.0058 |
| 2 | mmu-miR-143-3p_R + 1 | MIMAT0000247 | 140672.4247 | 92946.7573 | 0.0088 |
| 3 | mmu-miR-338-3p_R − 1 | MIMAT0000582 | 11771.9859 | 22578.0830 | 0.0112 |
| 4 | mmu-miR-219a-2-3p | MIMAT0022841 | 5764.2987 | 9115.6537 | 0.0131 |
| 5 | mmu-miR-221-5p_R − 4 | MIMAT0017060 | 7648.3178 | 1828.4888 | 0.0167 |
| 6 | mmu-miR-103-3p | MIMAT0000546 | 15123.6637 | 9885.3936 | 0.0210 |
| 7 | mmu-miR-744-5p_R − 1 | MIMAT0004187 | 13593.5815 | 7321.5200 | 0.0224 |
| 8 | mmu-miR-26b-5p_R + 1 | MIMAT0000534 | 22637.1354 | 30484.1688 | 0.0272 |
| 9 | mmu-miR-222-3p_R + 2 | MIMAT0000670 | 22167.7190 | 8430.5095 | 0.0316 |
| 10 | mmu-miR-26a-5p | MIMAT0000533 | 513205.9107 | 428165.3741 | 0.0323 |
| 11 | mmu-let-7d-5p | MIMAT0000383 | 81525.0144 | 50892.8572 | 0.0402 |
| 12 | mmu-miR-9-5p | MIMAT0000142 | 88155.5092 | 59575.7830 | 0.0405 |
| 13 | mmu-miR-378a-3p_R + 1 | MIMAT0003151 | 16043.4259 | 8933.7047 | 0.0443 |
| 14 | mmu-miR-330-3p_L − 1 | MIMAT0000569 | 7623.2540 | 3729.2710 | 0.0490 |
| | Reads less than average reads (7616) | | | | |
| 1 | mmu-miR-107-3p_R − 1 | MIMAT0000647 | 2906.1178 | 2349.9838 | 0.0018 |
| 2 | mmu-miR-664-3p_R − 1 | MIMAT0012774 | 1761.7548 | 1448.2006 | 0.0024 |
| 3 | mmu-miR-155-5p | MIMAT0000165 | 15.6553 | 89.1600 | 0.0039 |
| 4 | mmu-miR-8114 | MIMAT0031420 | 25.4082 | 47.9355 | 0.0042 |
| 5 | mmu-miR-142a-5p_L + 2R − 3 | MIMAT0000154 | 3604.1938 | 6352.3171 | 0.0052 |
| 6 | mmu-miR-216b-5p | MIMAT0003729 | 3.9138 | 15.9094 | 0.0055 |
| 7 | mmu-miR-181b-1-3p_R + 2 | MIMAT0017067 | 81.2203 | 103.0799 | 0.0057 |
| 8 | mmu-miR-7021-5p_L + 2R − 2 | MIMAT0027946 | 10.3621 | 5.1722 | 0.0059 |
| 9 | cgr-miR-1260_R + 2 | MIMAT0023746 | 130.0382 | 214.9477 | 0.0065 |
| 10 | mmu-miR-125b-1-3p | MIMAT0004669 | 1433.0540 | 2253.7315 | 0.0067 |
| 11 | mmu-miR-7047-3p | MIMAT0027999 | 52.3078 | 37.0068 | 0.0077 |
| 12 | mmu-miR-130b-3p | MIMAT0000387 | 27.2286 | 49.1028 | 0.0080 |
| 13 | mmu-miR-141-3p_R − 1 | MIMAT0000153 | 10.2573 | 75.7050 | 0.0080 |
| 14 | PC-3p-26288_26 | | 2.1494 | 8.8522 | 0.0090 |
| 15 | mmu-miR-7235-3p_R − 1 | MIMAT0028439 | 19.6812 | 11.5262 | 0.0092 |
| 16 | mmu-miR-181a-1-3p | MIMAT0000660 | 1993.9888 | 2240.8242 | 0.0093 |
| 17 | mmu-miR-669o-3p_R − 1 | MIMAT0017347 | 9.5920 | 12.8881 | 0.0097 |
| 18 | PC-5p-7215_175 | | 24.8939 | 79.1250 | 0.0111 |
| 19 | mmu-miR-7226-3p_R − 2 | MIMAT0028421 | 3.9138 | 8.8405 | 0.0116 |
| 20 | rno-miR-1843b-3p_1ss3TC | MIMAT0035731 | 350.6473 | 272.0225 | 0.0116 |
| 21 | mmu-miR-25-5p_R + 1 | MIMAT0017049 | 31.1985 | 20.0083 | 0.0120 |
| 22 | mmu-miR-29b-2-5p_R − 2 | MIMAT0017063 | 143.1201 | 105.6110 | 0.0133 |
| 23 | mmu-miR-124-5p | MIMAT0004527 | 155.9453 | 107.9933 | 0.0147 |
| 24 | PC-3p-23856_30 | | 19.5691 | 27.9148 | 0.0160 |
| 25 | mmu-miR-6540-3p | MIMAT0025586 | 4.7960 | 13.0985 | 0.0169 |
| 26 | mmu-miR-15a-3p_1ss22AT | MIMAT0004624 | 68.4602 | 105.0508 | 0.0184 |
| 27 | mmu-mir-16-1-p3 | | 93.8195 | 124.6812 | 0.0192 |
| 28 | ptr-miR-92_R + 2 | MIMAT0002699 | 803.6286 | 992.8661 | 0.0204 |
| 29 | ssc-mir-4335-p5 | | 105.0150 | 139.7552 | 0.0208 |

TABLE 4-continued

Differentially regulated microRNAs at 6 months

| # | Accession ID | Name | Ctrl-reads (mean) | Tau-reads (mean) | p-value |
|---|---|---|---|---|---|
| 30 | mmu-miR-671-3p | MIMAT0004821 | 924.0569 | 692.3528 | 0.0217 |
| 31 | tch-mir-9771b-p5__1ss14CG | | 28.0352 | 14.3503 | 0.0226 |
| 32 | mmu-miR-676-5p | MIMAT0003781 | 133.7766 | 117.8463 | 0.0236 |
| 33 | mmu-miR-1843b-5p__L + 1R − 1 | MIMAT0019345 | 5617.6345 | 4353.0472 | 0.0237 |
| 34 | hsa-miR-4792__L + 1R + 2__1ss10GT | MIMAT0019964 | 5.2931 | 30.7330 | 0.0248 |
| 35 | mmu-miR-362-3p__1ss22AT | MIMAT0004684 | 304.3179 | 386.2450 | 0.0251 |
| 36 | mmu-miR-188-3p | MIMAT0004541 | 27.0117 | 52.6916 | 0.0259 |
| 37 | mmu-miR-337-3p__L + 1R − 2 | MIMAT0000578 | 251.5418 | 602.0004 | 0.0263 |
| 38 | mdo-miR-150-5p__1ss21AT | MIMAT0012748 | 726.8891 | 981.7618 | 0.0281 |
| 39 | mmu-miR-21a-3p__R − 1 | MIMAT0004628 | 53.0146 | 114.2543 | 0.0282 |
| 40 | mmu-miR-411-3p__R − 1 | MIMAT0001093 | 410.0126 | 466.9449 | 0.0287 |
| 41 | efu-mir-9277-p3__2ss17AC18GA | | 206.6134 | 345.0022 | 0.0299 |
| 42 | mmu-miR-202-5p | MIMAT0004546 | 6.1753 | 14.9102 | 0.0300 |
| 43 | mmu-miR-1191b-5p | MIMAT0029866 | 4.6839 | 10.8738 | 0.0315 |
| 44 | mmu-miR-195a-5p | MIMAT0000225 | 4275.6671 | 2764.2947 | 0.0320 |
| 45 | mmu-miR-328-3p | MIMAT0000565 | 6894.2386 | 5161.2803 | 0.0321 |
| 46 | mmu-miR-193a-3p | MIMAT0000223 | 7.5547 | 23.6816 | 0.0330 |
| 47 | mdo-mir-7311-p5__1ss8CG | | 10.6351 | 26.3714 | 0.0341 |
| 48 | mmu-miR-219a-5p | MIMAT0000664 | 1856.5034 | 4047.0971 | 0.0348 |
| 49 | mmu-miR-7044-3p | MIMAT0027993 | 15.7044 | 5.8071 | 0.0350 |
| 50 | mmu-miR-28c__L + 1R + 1 | MIMAT0019339 | 37.5045 | 28.8722 | 0.0366 |
| 51 | oan-miR-1386__L − 1R − 1 | MIMAT0007162 | 19.8421 | 34.5650 | 0.0368 |
| 52 | mmu-miR-30c-1-3p | MIMAT0004616 | 164.9091 | 137.7552 | 0.0370 |
| 53 | mmu-miR-182-3p__L − 1 | MIMAT0016995 | 1.7644 | 6.6716 | 0.0372 |
| 54 | mmu-miR-216a-5p | MIMAT0000662 | 30.7990 | 110.6161 | 0.0397 |
| 55 | mmu-miR-1839-5p | MIMAT0009456 | 3565.2743 | 2244.8241 | 0.0397 |
| 56 | PC-3p-6216__220 | | 11.3076 | 67.6414 | 0.0405 |
| 57 | mmu-miR-676-3p | MIMAT0003782 | 2038.1113 | 1454.7540 | 0.0415 |
| 58 | mmu-miR-7a-1-3p | MIMAT0004670 | 626.8949 | 479.2330 | 0.0415 |
| 59 | mmu-miR-93-5p__R − 2 | MIMAT0000540 | 1422.9805 | 2062.6838 | 0.0423 |
| 60 | mmu-miR-504-5p | MIMAT0004889 | 206.0330 | 113.5930 | 0.0429 |
| 61 | mmu-miR-150-5p__R − 1 | MIMAT0000160 | 3439.2879 | 6305.0996 | 0.0439 |
| 62 | chi-miR-30a-3p__L-1R + 2 | MIMAT0036122 | 17.5317 | 27.4896 | 0.0439 |
| 63 | miR-1249-3p | MIMAT0010560 | 1807.8838 | 2515.4197 | 0.0445 |
| 64 | mmu-miR-5129-5p__R − 1__1ss12TC | MIMAT0020640 | 14.2271 | 4.0839 | 0.0446 |
| 65 | mmu-miR-142a-3p__R − 1 | MIMAT0000155 | 137.5440 | 303.5018 | 0.0447 |
| 66 | mmu-miR-139-3p__R + 1 | MIMAT0004662 | 1100.7157 | 678.1925 | 0.0448 |
| 67 | efu-mir-127-p5__1ss11CG | | 5.6782 | 8.6156 | 0.0452 |
| 68 | rno-mir-6320-p3__1ss15AC | | 98.9373 | 44.4195 | 0.0454 |
| 69 | mmu-miR-344d-3-5p | MIMAT0014807 | 352.5488 | 126.0435 | 0.0460 |
| 70 | mmu-miR-153-5p__L + 5 | MIMAT0016992 | 439.8190 | 337.1094 | 0.0461 |
| 71 | mmu-miR-195a-3p | MIMAT0017000 | 89.5207 | 59.8487 | 0.0465 |
| 72 | mmu-miR-450a-5p | MIMAT0001546 | 489.0501 | 373.8491 | 0.0466 |
| 73 | mmu-miR-351-5p__R − 1 | MIMAT0000609 | 1900.5414 | 1269.7919 | 0.0468 |
| 74 | mmu-miR-412-3p__L + 1 | MIMAT0001094 | 49.7733 | 28.1056 | 0.0470 |
| 75 | mmu-miR-551b-5p | MIMAT0017236 | 67.6557 | 34.6577 | 0.0476 |
| 76 | mmu-miR-1843a-3p__R − 1 | MIMAT0014806 | 132.8384 | 119.0427 | 0.0481 |
| 77 | PC-3p-12459__77 | | 11.6294 | 18.0646 | 0.0486 |
| 78 | mmu-miR-299b-3p__R + 4 | MIMAT0022837 | 163.5641 | 140.8624 | 0.0499 |

Selected miRs were experimentally validated by qPCR analysis. For 2 m, miR142-3p, miR181b, miR181a (also known as miR213) and miR219-5p were validated; and for 6 m, validation was performed for miR142-3p, miR142-5p, miR339 and miR1249.

miR-RNA Pairing Analysis to Identify Putative miR Targets and Pathways in Tau Hippocampi at a Presymptomatic Stage In order to correlate the global effect on gene expression that, in part, is contributed by miR alterations in the Tau hippocampus, we performed mRNA sequencing with 2 m hippocampi. A multi-dimensional scaling (MDS) plot, assessing the similarities/differences among the expression profiles, shows clear separation between control and Tau hippocampi. The differential expression (DE) analysis identified 254 upregulated and 258 downregulated genes (FDR<0.05). qPCR experiments validated the differential expression levels of the following genes: Prion Protein (Prnp), Complement C4B (C4b) and Triggering Receptor Expressed on Myeloid Cells 2 (Trem2).

Ingenuity Pathway Analysis (IPA) (Ingenuity H Systems, www.ingenuity.com) was then used for network analysis to correlate the observed transcriptomic changes to underlying Canonical Pathways, Transcriptomic Networks, and Disease Biofunctions. The top canonical signaling pathway revealed by IPA analysis corresponds to "Neuroinflammation Signaling Pathway", which includes Interleukin 6 Receptor (IL6R), Trem2 and Colony-Stimulating Factor 1 Receptor (Csf1r) as key genes. Inflammatory Response, Cell-To-Cell Signaling and Interaction, Cellular Function and Maintenance network was identified as one of the top 5 transcriptomic networks. This network includes Csf3r, Interferon alpha/beta (Ifn-alpha/beta) and Trem2, key genes involved in inflammation.

Next, we conducted miR-mRNA pairing analysis to assess the potential transcriptome changes resulted from miR-alterations in 2 m Tau hippocampi. Specifically, IPA analysis was conducted to examine the overlap between miR-targets, identified by IPA's "microRNA Target Filter"

feature, and differentially changed mRNAs from 2 m Tau hippocampi, identified by RNA sequencing. IPA "microRNA Target Filter" predicted miR targets with data collected in TargetScan's human predicted target dataset, and experimentally validated targets from TarBase. This pairing analysis found 72 miRNAs pair with 401 gene targets. Pathway analysis of these overlapping targets revealed that "Neuroinflammation Signaling Pathway" is the top canonical pathway, "Neurological Disease" is the top disease in disease and biofunctions, and "Cell-To-Cell Signaling and Interaction, Cellular Movement, Hematological System Development and Function" is the top transcriptomic network. In addition to "Neuroinflammation Signaling Pathway", several other canonical pathways involved in inflammation and immune response were also altered, such as "Fcγ Receptor-mediated Phagocytosis in Macrophages and Monocytes" and "Role of NFAT in Regulation of the Immune Response".

MiR142 is Significantly Induced in the Hippocampus and Cortex of Tau Mice

MiR142-3p has been shown to regulate the neuroinflammation associated with Multiple Sclerosis (Mandolesi, G. et al. J Neurosci 37, 546-561, (2017). Upregulation of both miR142-3p and -5p was reported in the prefrontal cortex of LOAD patients (Lau, P. et al. EMBO Mol Med 5, 1613-1634, (2013). miR181a and miR181b are involved in alteration of synaptic plasticity associated with neuropathology in a murine model of AD (Rodriguez-Ortiz et al. J Alzheimers Dis 42, 1229-1238, (2014). Santa-Maria et al. showed that miR219 represses Tau synthesis at the post transcriptional level (Santa-Maria, I. et al. J Clin Invest 125, 681-686, (2015). Thus, we prioritized miR142-3p, miR142-5p, miR181a, miR181b, miR219-3p and miR219-5p to examine their temporal expression profiles in control and Tau hippocampi.

Figure 1B:
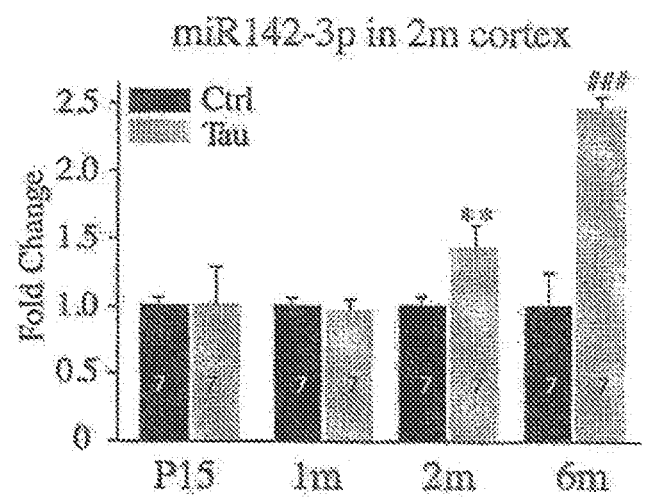

In Tau mice, Tau(P301L) is driven by CaMKIIα-tTA and begins to express around postnatal day 7. To examine whether miR changes occurred shortly after Tau(P301L) overexpression, we performed qPCR to determine the temporal expression profiles of miRs in control mice without CaMKIIα-tTA or hTau(P301L) transgenes and Tau hippocampi at postnatal day 15, 1 m, 2 m and 6 m (FIG. 1A). The expression of miR142-3p was induced at postnatal day 15 and persisted until 6 m. Thus, the upregulation pattern of miR142-3p correlates well with the time course of Tau (P301L) overexpression (OE). The upregulation of miR142-5p, miR181b, miR219-3p and miR219-5p became significant at 1 m (FIG. 1A). Tau mice carry one copy of CaMKIIα-tTA and one copy of hTau transgene. Previous reports have shown that CaMKIIα-tTA mice also exhibit neurodegeneration and behavioral phenotypes. To determine whether a single CamKIIα-tTA or hTau transgene OE can cause miR142-3P upregulation, we conducted qPCR experiments with 2 m hippocampi from CamKIIα-tTA-only and hTau transgene-only mice. No significant differences in miR142-3p levels were observed among control mice containing neither transgene or only one of the two transgenes, confirming that CaMKII-tTA transgene alone has no effect on miR142-3p expression. In addition to hippocampus, we found that miR142-3p expression is induced in Tau cortex at 2 m and 6 m (FIG. 1B).

Figure 2:
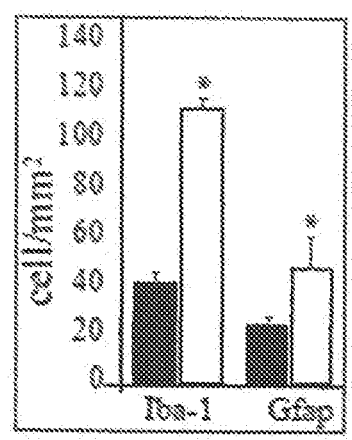
FIG. 2 depicts data showing that sustained in vivo miR-142 gain of function as produced in MiR142-OE results in increased microglia and astrocyte cell types in cortical neurons. The associated increase of microglia (Iba1 staining) and astrocytes (Gfap staining) in the cortex of miR142-OE vs tdTomato controls is shown in the bar graph comparing detected immunofluorescence of miR142-OE vs tdTomato control.

To determine whether miR142 is expressed in neurons or microglia, we performed in situ hybridization (ISH) with anti-miR142-5p DNA probe in combination with immunostaining (IHC) using NeuN (recognizing neurons) and Iba-1 (recognizing microglia) antibodies. We chose to examine miR142-5p because it is expressed at higher levels than miR142-3p based on small RNA sequencing data. Dual ISH and IHC staining was performed on the coronal brain sections from 3 Tau animals with 3 littermate controls. The specificity of this experiment was verified with two positive controls: (1) spleen was used as the positive control for its high levels of miR142-5p; (2) U6, a noncoding snRNA, was used as additional probe control for all tissues because it is present in most cell types. We found that miR142-5p was more abundant in 6 m Tau hippocampi compared to control. Strong miR142-5p signals could be detected in both NeuN$^+$ neurons and Iba-1$^+$ microglia in Tau hippocampi CA1 area (FIG. 2). As previously reported, we also detected more Iba-1 immunoreactivity in Tau hippocampi. This finding is consistent with previous studies showing that miR142-5p and -3p are expressed in both neurons and myeloid cell types in the hippocampus of simian immunodeficiency virus encephalitis brains.

Figure 3:
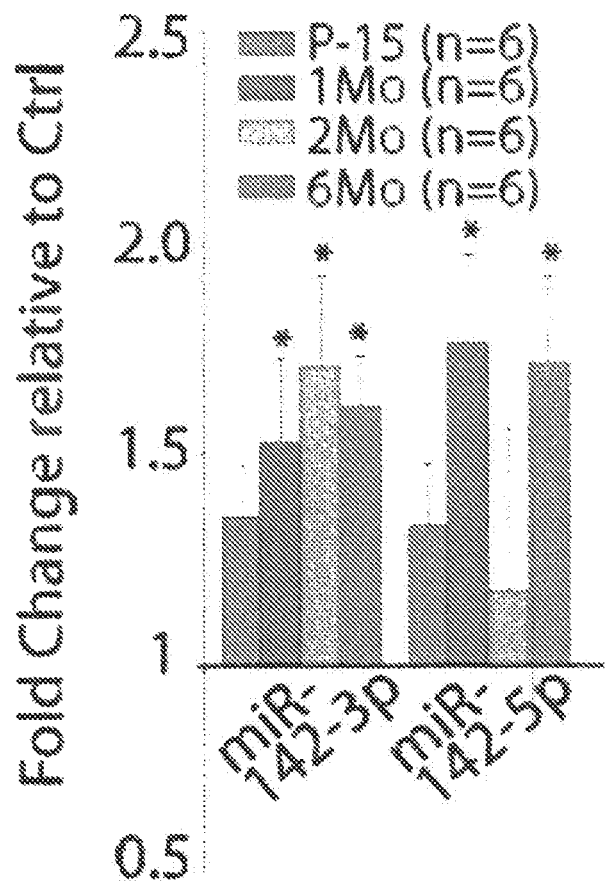
FIG. 3 presents data demonstrating that miR-142 expression levels are increased in tau mice brains. qPCR analysis for miR-142-3p and -5p expression levels relative to control brain samples from 2 weeks to 6 months demonstrates significant enhanced expression at 1 month to 6 months.

Neuronal miR142 Overexpression in Developing Cortex of Wildtype Brain Leads to Many Transcriptional Changes The early and persistent miR142 upregulation in Tau hippocampi, and its involvement in the inflammatory axis prompted our investigation of its direct impacts on gene transcription. The in utero electroporation (IUE) technique is a widely used technique to deliver gene expression constructs into cortical neurons at late embryonic stages. Here we employed IUE to introduce miR142 or control expression cassette into cortical neurons to assess the impact of miR142-OE on the cortical transcriptome at 1 m. Specifically, we electroporated miR142 together with GFP-reporter or with a tdTomato-reporter expression cassette alone (served as control) into the developing cortical plate of wildtype embryos at embryonic day 14.5 (E14.5) and let these embryos developed to term for birth. Using double-immunostaining with 1 m miR142-OE brains, we found that the majority of GFP-positive cells were also NeuN-positive (neuronal marker) but not S100β-positive (astrocyte marker). qPCR analysis revealed a modest but significant increase in miR142 (-5p, 1.2 fold; and -3p, 1.4 fold) expression in the cortex prepared from miR142OE when compared with control cortices (FIG. 3).

To assess transcriptome changes induced by miR142-OE in cortical neurons at 1 m, we performed mRNA sequencing on miR142-OE (GFP-positive) versus control (tdTomato-positive) cortices. The MDS plot obtained after mRNA-seq shows clear separation between miR142-OE and control samples. miR142-OE caused significant downregulation of 641 genes and upregulation of 501 genes (FDR<0.05). The gene network and pathway analysis found that the top transcriptomic network altered by miR142-OE is "Cellular Assembly and Organization, Cellular Function and Maintenance, Cellular Movement". The top canonical pathways, and top diseases and biofunctions altered by miR142-OE were also analyzed. These data provide the first in vivo demonstration that miR142-OE in cortical neurons can lead to substantial transcriptional changes.

Overlapping Gene Expression Changes Between miR142 and Tau Overexpression

Comparison of gene changes in miR142-OE and Tau-OE, based on the mRNA-seq data presented above, revealed 11 upregulated and 22 downregulated genes common between two datasets (Table 5).

TABLE 5

Common genes between tau and miR142-OE RNA-seq data

| Up-regulated genes | Up-regulated gene names | Down-regulated genes | Down-regulated gene names |
|---|---|---|---|
| Gfap | Glial Fibrillary Acidic Protein | Esyt2 | Extended Synaptotagmin 2 |
| Islr2 | Immunoglobulin Superfamily Containing Leucine Rich Repeat 2 | Grm4 | Glutamate Metabotropic Receptor 4 |
| Csf1 | Colony Stimulating Factor 1 | Scn4b | Sodium Voltage-Gated Channel Beta Subunit 4 |
| Wnt7b | Wnt Family Member 7B | Pcp4l1 | Purkinje Cell Protein 4 Like 1 |
| Trpv2 | Transient Receptor Potential Cation Channel Subfamily V Member 2 | Nexn | Nexilin F-Actin Binding Protein |
| Anxa7 | Annexin A7 | Kcnh4 | Potassium Voltage-Gated Channel Subfamily H Member 4 |
| Fgf5 | Fibroblast Growth Factor 5 | Rasd2 | RASD Family Member 2 |
| Tmem178 | Transmembrane Protein 178A | Unc13c | Unc-13 Homolog C |
| Rxfp1 | Relaxin/Insulin Like Family Peptide Receptor 1 | Calb1 | Calbindin 1 |
| Pde1a | Phosphodiesterase 1A | Pdzd2 | PDZ Domain Containing 2 |
| Clcnka | Chloride Voltage-Gated Channel Ka | Myh7 | Myosin Heavy Chain 7 |
|  |  | Strip2 | Striatin Interacting Protein 2 |
|  |  | Pde7b | Phosphodiesterase 7B |
|  |  | Dach1 | Dachshund Family Transcription Factor 1 |
|  |  | Stc1 | Stanniocalcin 1 |
|  |  | Pou3f4 | POU Class 3 Homeobox 4 |
|  |  | Ptprv | Protein Tyrosine Phosphatase, Receptor Type V |
|  |  | Slc32a1 | Solute Carrier Family 32 Member 1 |
|  |  | Per3 | Period Circadian Clock 3 |
|  |  | Scarb1 | Scavenger Receptor Class B Member 1 |
|  |  | Kcnj2 | Potassium Voltage-Gated Channel Subfamily J Member 2 |
|  |  | Gpr88 | G Protein-Coupled Receptor 88 |

Among the upregulated genes, both Gfap and Csf1 are known to play key roles in inflammation and gliosis. GFAP is considered a marker of astrogliosis while CSF1 controls the development and functions of macrophages, such as microglia. Mutations in the Csf1r gene are associated with progressive dementia and inhibiting CSF1R increases disease severity in animal models of AD. We validated these changes using qPCR in both miR142-OE cortex and Tau OE hippocampus. Interestingly, applying lentivirus vector carrying miR142-3p expressing cassette to in-vitro (DIV7) primary cortical neurons also led to Gfap and Csf1 upregulation at DIV11 in addition to the increase of miR142-3P.

To assess whether miR142-OE in cortical neurons could lead to infiltration or proliferation of microglia and astrocytes in miR142-OE cortex, we performed immunostaining using Iba-1 and GFAP antibodies. Significant increases in Iba-1 positive microglia and GFAP-positive reactive astrocytes were observed in miR142-OE cortical regions compared to tdTomato controls (FIG. 2). This observation suggests that miR142-OE in neurons could elicit inflammatory signals that lead to an increase in microglia and reactive astrocytes numbers.

MiR142-OE Exerts Similar Effect as Tau-OE on Biological and Disease Networks

Overlapping gene expression changes between miR142 and Tau OE prompted us to examine the contributory role of miR142 to the gene networks and disease pathways caused by Tau-OE. To assess this, we compared the canonical pathways as well as disease and biological functions between miR142-OE and Tau-OE samples. Even though miR142-OE and Tau-OE models target several different genes, a high degree of directional similarity in the pathway regulation was observed between the two groups. With respect to inflammatory pathways, the canonical pathways that were similarly changed include signal transducer and activator of transcription 3 (Stat3) pathway and tumor necrosis factor receptor 2 (Tnfr2) signaling. Stat3 is a transcription factor involved in cytokine mediated signaling pathways and its activation promotes astrogliogenesis associated with brain inflammation. Upon TNF binding, Tnfr2 can activate apoptosis and inflammation. Disease and biological functions also revealed similar and robust changes in macrophage migration, movement and phagocytosis, suggesting an increase in inflammatory signals.

Discussion

Here we identified several miRs that are altered in both the presymptomatic and symptomatic stages of tauopathy. To explore whether miR changes can result in the gene expression alterations observed in Tau-OE, we explored the predicted targets of the differentially expressed miRs and compared the overlap between these predicted targets and the mRNA changes in 2 m Tau hippocampi. Subsequent pathway analysis of the overlapping genes identified several important signaling pathways, with neuroinflammation as the top pathway. Using the IUE surgical technique, we were able to provide the first in vivo demonstration that neuronal miR142-OE in wildtype cortex leads to gliosis as well as dysregulation of genes involved in several disease pathways. Many of these processes are also altered in Tau hippocampi, such as inflammation. The upregulation of Gfap and Csf1 mRNA levels in miR142-OE cortex or Tau(P301L) OE hippocampi are likely to cause the increase of microglia and reactive astrocytes. Taken together, our data provides evidence that Tau-OE induces presymptomatic miR-changes and such miR alterations are likely to mediate alterations in gene regulatory networks, and disease and biological pathways.

Previous transcriptional analysis with mouse tauopathy models has revealed pathways in neuronal function, cell metabolism, signal transduction and stress response at symptomatic ages. Here we found significant mRNA changes in Tau hippocampi as early as 2 m. Interestingly, the expression changes of genes such as Gfap, Csf1, Prnp, C4b and Trem2, identified with 2 m Tau hippocampi have been observed at symptomatic stages in the same rTg4510 tauopathy model in other studies. These genes are involved in various aspects of inflammatory responses and neurodegeneration. Astrocyte reactivity, which is characterized by Gfap overexpression, contributes to many neurodegenerative diseases. Meta-analysis of gene expression studies to identify common transcriptomic signatures for neurodegenerative diseases has identified Csf1 as one common inflammatory marker. Prnp has been implicated as a causative protein agent in tauopathies and many neurological disorders including AD, Parkinson's disease, Lou Gehrig's disease and Creutzfeldt-Jakob disease. Complements are known in modulating the inflammatory axis in many neurodegenerative disorders. Dysregulated Trem2 signaling in microglia has been shown to be involved in both Tau and amyloid pathology, most likely by mediating microglial responses to neuroinflammation.

Several predicted miR-regulated genes from our miR-RNA pairing analysis are involved in the inflammatory response, such as Trem2, Csf1r, Il6r, Phosphatidylinositol-4,5-Bisphosphate 3-Kinase Catalytic Subunit Gamma (Pik3cg), Ras-Related C3 Botulinum Toxin Substrate 2 (Rac2), and Tgfβ receptor 1/2. Aberrant expression of Rac2 has been reported in the pathogenesis of childhood pre-B-cell acute lymphoblastic leukemia in a mouse model[66]. Enhanced Tgfβ signaling following brain injury has been shown to alter immune function in brain pericytes by attenuating the expression of several chemokines and adhesion molecules. miR-mRNA pairing analysis also revealed several miR gene targets involved in Neuroinflammation, Complement System, cAMP-mediated signaling, and G-Protein Coupled Receptor (GPCR) Signaling. Many complement proteins, including components of C1q, are important mediators of inflammatory response in several neurodegenerative disorders such as AD, Parkinson's disease, Huntington's disease and Prion diseases. Altered cAMP-mediated signaling has been shown in many neurodegenerative diseases. Many components of this pathway including cAMP, protein kinase, PKA and cyclic AMP response element-binding protein (Creb) are implicated in Tau phosphorylation and neurofibrillary tangles as well as cognitive decline in AD. Studies have explored the involvement of GPCRs in the progression of AD. Mechanisms involved in the regulation of expression, degradation and trafficking of BACE1, a key enzyme in AD pathogenesis, by GPCRs have provided insights into the pathophysiology of AD as well as development of potential therapeutic modalities.

MiR142 is an evolutionary conserved pre-miR that encodes for two separate miRs, miR142-3p and miR142-5p. Both miRs are co-transcribed, and share many common targets. However, post-transcriptional regulation may account for their differential expression levels observed in our sequencing dataset (GSE106967). Several studies have delineated the role of miR142 in immune responses in multiple pathological conditions. We found that miR142 (-3p and -5p) induction occurs soon after Tau(P301L) OE triggered by CaMKIIα-tTA, and it persists through later stages. Many cytokines and inflammation associated molecules have been characterized as direct or indirect targets of miR142, suggesting its quintessential role in inflammatory processes. miR142 alteration has also been associated with many pathological conditions, such as cardiomyopathy, atherosclerosis, osteoarthritis and chronic fibrosis. A recent study highlighted the role of miR142 in multiple sclerosis (MS), a neurodegenerative disease characterized by immune system dysfunction.

Here, we provide experimental evidence that neuronal miR142-OE in wildtype brains upregulates expression of many inflammatory genes accompanied by an increase of microglia and reactive astrocytes.

The miR-mediated modulation of a cohort of genes that lie upstream of signaling pathways, may lead to robust effects even with subtle changes in miR expression. Similar effects were observed in our study, where modest miR142 overexpression in cortical neurons resulted in widespread transcriptome changes. Interestingly, both miR142 OE and Tau OE induced many genes involved in inflammation, including Gfap and Csf1. This was also manifested in the altered regulation at the level of gene networks and pathways. Both miR142-OE and Tau-OE induced Stat3 and Tnfr2 signaling pathways. In addition, disease functions involved in the migration of cell types implicated in inflammation, including macrophages were elevated. Thus, manipulating a single miR, such as miR142, can lead to profound changes in biological pathways contributing to neurodegeneration. Therefore, this study shows that the early miR changes that can occur in tauopathies have pathological consequences.

In summary, we found many canonical and disease associated pathways that are altered at the presymptomatic stage of tauopathy. Many of these pathways could be altered by miR-changes as revealed by pairing of predicted miR targets with RNAseq-validated mRNA changes. As proof-of-concept, we show that miR142-OE in cortical neurons is sufficient to trigger changes in many gene network pathways, including inflammation. Several of these pathways are also altered in presymptomatic stages of tauopathy in Tau animal model. Thus, our data provide strong support for the early miR changes triggered by Tau(P301L) expression and how these changes may impact the disease progression by altering several key biological pathways.

The invention claimed is:

1. A method of treating neuroinflammation in a patient having a neurodegenerative condition and exhibiting elevated levels of two or more micro RNAs selected from the group consisting of miR142-3p, miR142-5p, and miR219-3p, said method comprising:
   identifying in patients having a neurodegenerative condition, those patients having elevated levels of two or more micro RNAs selected from the group consisting of miR219-3p, miR142-3p and miR142-5, by
   i) obtaining a reference expression level of two or more micro RNAs selected from the group consisting of miR219-3p, miR142-3p and miR142-5p;
   ii) determining an expression level of two or more micro RNAs selected from the group consisting of miR219-3p, miR142-3p and miR142-5p, and corresponding to those of step i), in a sample obtained from said patient having a neurodegenerative condition, wherein an increase in the expression level of said two or more micro RNAs selected from the group consisting of miR142-3p and miR142-5p in said patient's sample as compared to the reference expression level identifies the patient as having neuroinflammation; and
   administering to said patient having a neurodegenerative condition and identified as having elevated levels of said two or more micro RNAs selected from the group consisting of miR142-3p, miR142-5p, and miR219-3p a therapeutic composition comprising an antisense or interference oligonucleotide that is complementary to a micro RNA selected from the group consisting of miR142-3p, miR142-5p, and miR219-3p, wherein said antisense or interference oligonucleotide reduces the expression of a micro RNA selected from the group consisting of miR219-3p, miR142-3p and miR142-5p and provides treatment of said neuroinflammation.

2. A method of treating neuroinflammation in a patient with a neurodegenerative condition, said method comprising
   i) obtaining a reference expression level of miR142-3p and miR219-3p;
   ii) determining an expression level of miR142-3p and miR219-3p, in a sample obtained from said patient, wherein an increase in the expression level of miR142-3p and miR219-3p in said patient's sample as compared to the reference expression level identifies the patient as having neuroinflammation; and
   administering a therapeutic composition comprising antisense or interference oligonucleotides that are complementary to the sequence of miR142-3p and miR219-3p to reduce the expression of miR142-3p and miR219-3p and treat said neuroinflammation.

3. The method of claim 2 further comprising the steps of
   iii) obtaining a reference expression level of a micro RNA selected from the group consisting of miR142-5p, miR181a, miR181b, and miR219-5p;
   iv) determining an expression level of a micro RNA selected from the group consisting of miR142-5p, miR181a, miR181b, and miR219-5p, in said test patient's sample, wherein an increase in the expression level of one or more of miR142-5p, miR181a, miR181b, and miR219-5p in said test patient's sample as compared to the reference expression level, in addition to the detected increase in expression levels of miR142-3p and miR219-3p, identifies the patient as having neuroinflammation.

* * * * *

SEQUENCE LISTING

<160> NUMBER OF SEQ ID NOS: 10

<210> SEQ ID NO 1
<211> LENGTH: 21
<212> TYPE: RNA
<213> ORGANISM: Mus musculus

<400> SEQUENCE: 1
cauaaaguag aaagcacuac u                    21

<210> SEQ ID NO 2
<211> LENGTH: 23
<212> TYPE: RNA
<213> ORGANISM: Mus musculus

<400> SEQUENCE: 2
uguaguguuu ccuacuuuau gga                  23

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
agctttctca gccattcg                                                18

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
acaaaggtcc cacttgga                                                18

<210> SEQ ID NO 5
<211> LENGTH: 17
<212> TYPE: DNA
<213> ORGANISM: Artificial Sequence
<220> FEATURE:
<223> OTHER INFORMATION: Synthetic

<400> SEQUENCE: 5
tcggccctaa gggtact                                                 17

<210> SEQ ID NO 6
<211> LENGTH: 18
<212> TYPE: DNA
<213> ORGANISM: Artificial Sequence
<220> FEATURE:
<223> OTHER INFORMATION: Synthetic

<400> SEQUENCE: 6
tgcgtggctc atagttct                                                18

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
attacaaccc aagcacagg                                               19

<210> SEQ ID NO 8
<211> LENGTH: 18
<212> TYPE: DNA
<213> ORGANISM: Artificial Sequence
<220> FEATURE:
<223> OTHER INFORMATION: Synthetic

<400> SEQUENCE: 8
gacctgcttg ctgttgaa                                                18

<210> SEQ ID NO 9
<211> LENGTH: 20
<212> TYPE: DNA
<213> ORGANISM: Artificial Sequence
<220> FEATURE:
<223> OTHER INFORMATION: Synthetic

```
<400> SEQUENCE: 9
tgcaccacca actgcttagc                                            20

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
ggcatggact gtggtcatga g                                          21
```